US012691180B2

(12) United States Patent
Lopez et al.

(10) Patent No.: US 12,691,180 B2
(45) **Date of Patent: *Jul. 28, 2026**

(54) METHODS OF IMPROVING TOLERABILITY, PHARMACODYNAMICS, AND EFFICACY OF BETA-ALANINE AND USE THEREFOR

(71) Applicant: CarnoCo, LLC, Millstone, NJ (US)

(72) Inventors: Hector L. Lopez, Cream Ridge, NJ (US); Timothy N. Ziegenfuss, Chardon, OH (US)

(73) Assignee: CarnoCo, LLC, Millstone, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,838

(22) Filed: Nov. 19, 2018

(65) Prior Publication Data

US 2019/0151459 A1 May 23, 2019

Related U.S. Application Data

(63) Continuation of application No. 14/349,772, filed as application No. PCT/US2014/013431 on Jan. 28, 2014, now Pat. No. 10,130,715.

(60) Provisional application No. 61/757,604, filed on Jan. 28, 2013.

(51) Int. Cl.

| | |
|---|---|
| *A61K 47/00* | (2006.01) |
| *A23L 33/175* | (2016.01) |
| *A61K 31/197* | (2006.01) |
| *A61K 31/198* | (2006.01) |
| *A61K 33/06* | (2006.01) |
| *A61K 36/37* | (2006.01) |
| *A61K 36/69* | (2006.01) |
| *A61K 36/725* | (2006.01) |
| *A61K 36/882* | (2006.01) |
| *A61K 45/06* | (2006.01) |
| *A61K 47/54* | (2017.01) |
| *A61K 47/55* | (2017.01) |

(52) U.S. Cl.

CPC ............ *A61K 47/55* (2017.08); *A23L 33/175* (2016.08); *A61K 31/197* (2013.01); *A61K 31/198* (2013.01); *A61K 33/06* (2013.01); *A61K 36/37* (2013.01); *A61K 36/69* (2013.01); *A61K 36/725* (2013.01); *A61K 36/882* (2013.01); *A61K 45/06* (2013.01); *A61K 47/542* (2017.08); *A23V 2002/00* (2013.01)

(58) Field of Classification Search

CPC .... A61K 47/55; A61K 47/542; A61K 31/197; A61K 31/198; A61K 33/06; A61K 36/37; A61K 36/69; A61K 36/725; A61K 36/882; A61K 45/06; A23L 33/175; A23V 2002/00

See application file for complete search history.

(56) References Cited

U.S. PATENT DOCUMENTS

| | | | | |
|---|---|---|---|---|
| 4,021,536 A | | 5/1977 | Rubino | |
| 6,150,419 A | * | 11/2000 | Fairbanks | A61K 31/155 514/634 |
| 10,130,715 B2 | | 11/2018 | Lopez | |
| 2004/0059003 A1 | | 3/2004 | Mermelstein et al. | |
| 2006/0199237 A1 | * | 9/2006 | Smith | G01N 33/9406 435/7.92 |
| 2011/0123654 A1 | | 5/2011 | Jaeger et al. | |
| 2011/0250340 A1 | | 10/2011 | Johns | |
| 2012/0073001 A1 | | 3/2012 | Dong et al. | |
| 2012/0264826 A1 | | 10/2012 | Kramer et al. | |
| 2015/0182479 A1 | * | 7/2015 | Glynn | A61K 9/0043 514/634 |

FOREIGN PATENT DOCUMENTS

| | | | | |
|---|---|---|---|---|
| CN | 101455736 | | 6/2009 | |
| JP | 2006028174 | | 2/2006 | |
| WO | WO 1994/022483 | | 10/1994 | |
| WO | WO 2004/091497 A2 | | 10/2004 | |
| WO | WO 2005/079773 A2 | | 9/2005 | |
| WO | WO 2007/073398 A2 | | 6/2007 | |
| WO | WO-2010017405 A1 | * | 2/2010 | A61K 31/13 |

(Continued)

OTHER PUBLICATIONS

Strong et al. NMDA receptor modulators: an updated patent review, 2014, Expert Opinion on Therapeutic Patents, v. 24, pp. 1349-1366 (Year: 2014).*

Decombaz et al "Effect of slow-release beta-alanine tablets on absorption kinetics and paresthesia" (Amino Acids Jul. 2012 vol. 43: pp. 67-76). (Year: 2012).*

Lim et al (Biomol Thera 2012 vol. 20 No. 5: pp. 477-481). (Year: 2012).*

Fairbanks et al.(PNAS Sep. 12, 2000 vol. 97, No. 19, pp. 10584-10589.) (Year: 2000).*

Fallon (Year: 2013).*

Jensen et al 2001 (Year: 2001).*

Pregabalin (Year: 2007).*

Collins et al (Year: 2010).*

Kobota et al (Year: 2005).*

(Continued)

*Primary Examiner* — Catherine S Hibbert

(74) *Attorney, Agent, or Firm* — Morse, Barnes-Brown & Pendleton, P.C.; Lisa M. Warren, Esq.

(57) ABSTRACT

The present invention relates in some aspects to compositions (e.g., pharmaceutical, nutritional compositions, etc.), formulations, and food or beverage products comprising, consisting essentially of, or consisting of (a) β-alanine or a derivative of β-alanine, and (b) at least one agent that inhibits the N-methyl D-aspartate (NMDA) pathway or a pathway which converges downstream with the NMDA pathway. The compositions, formulations, and food or beverage products are useful for enhancing physical performance, reducing β-alanine-induced paraesthesia, and improving tolerance and compliance to higher doses of β-alanine, thereby reducing the length of time it takes to achieve peak effect of β-alanine, and increasing the magnitude of peak effect on physical performance in a human or animal.

11 Claims, 8 Drawing Sheets

(56) References Cited

FOREIGN PATENT DOCUMENTS

| | | |
|---|---|---|
| WO | WO 2011/019348 A1 | 2/2011 |
| WO | WO 2012/024611 | 2/2012 |
| WO | WO 2013/056048 A2 | 4/2013 |

OTHER PUBLICATIONS

Brill S. et al. "Efficacy of intravenous magnesium in neuropathic pain". British Journal of Anaesthesia, 89(5): 711-714 (2002).

Liu, et al., "Mechanisms of itch evoked by β-alanine," J. Neurosci 32(42): 14532-14537 (2012).

Liu, et al., "Sensory neuron-specific GPCRs Mrgprs are itch receptors mediating chloroquine-induced pruritus," Cell 139(7): 1353-1365 (2009).

Shinohara, et al., "Identification of a G Protein-coupled Receptor Specifically Responsive to β-Alanine*," The Journal of Biological Chemistry 279(22): 23559-23564 (2004).

Han, et al., "A subpopulation of nociceptors specifically linked to itch," Nat Neurosci 16(2): 174-182 (2013).

Genius et al., "Creatine Protects against Excitoxicity in an In Vitro Model of Neurodegeneration," *PLoS One*, 7(2):1-8, (Feb. 2012).

Sale et al., "Effect of beta-alanine supplementation on muscle carnosine concentrations and exercise performance," *Amino Acids*, 39:321-333, (2010).

Uno, et al., "Identification of Physiologically Active Substances as Novel Ligands for MRGPRD," *Journal of Biomedicine and Biotechnology*, 2012(Article ID 816159): pp. 1-9, (2012).

Deeb, et al. "Vitamin D signalling pathways in cancer: potential for anticancer therapeutics." Nature Reviews Cancer 7.9 (2007): pp. 684-700.

International Search Report for International Application PCT/US2014/013431, dated Jun. 5, 2014.

International Preliminary Report on Patentability for International Application PCT/US2014/013431, dated Jan. 14, 2015.

Extended Supplementary European Search Report from European Application No. EP 14 74 3168, dated Jun. 13, 2016.

Nurminen, et al. "Handgrip strength and balance in older adults following withdrawal from long-term use of temazepam, zopiclone or zolpidem as hypnotics," BMC Geriatrics, vol. 14, No. 121 pp. 1-10 (2014).

Peklar, et al. "Sedative Load and Frailty Among Community-Dwelling Population Aged ≥ 65 Years" Jamda 16 (2015) 282-289.

* cited by examiner

METHODS OF IMPROVING TOLERABILITY, PHARMACODYNAMICS, AND EFFICACY OF BETA-ALANINE AND USE THEREFOR

RELATED APPLICATIONS

This application is a continuation of U.S. application Ser. No. 14/349,772, filed Apr. 4, 2014, (now U.S. Pat. No. 10,130,715) which is a national stage filing under 35 U.S.C. 371 of International Application No. PCT/US2014/013431, filed Jan. 28, 2014, which claims the benefit of U.S. Provisional Application No. 61/757,604, filed on Jan. 28, 2013. The entire teachings of the above applications are incorporated herein by reference.

BACKGROUND OF THE INVENTION

It has been suggested that the anaerobic working capacity of tissues can be increased by ingesting either β-alanine, or a mixture of β-alanine and creatine (Harris and Dunnett, 1997; Stellingwerff et al., 2007). By increasing concentrations of β-alanine, the hope is to increase the biosynthesis of β-alanyl-L-histidine (carnosine) dipeptides, subsequently increasing the accumulation of carnosine in the body's tissues (Derave et al., 2007; Harris et al. 2007; Hill et al., 2007; Stout et al., 2007). Based on this supposition, β-alanine is sometimes included in pre-workout or post-workout dietary supplements or multivitamin preparations, especially those targeted at consumers who wish to improve muscular performance for training or competition, decrease fatigue, augment muscle bulk or strength, and enhance adaptations to exercise. However, when taken orally for improving exercise performance and capacity, β-alanine may cause sensory paraesthesia when ingested in amounts above 10 mg/kg body weight. These "pins and needles" and/or "intense itching" sensations are relatively mild at 10 mg/kg, but become severe at oral doses of 40 mg/kg (Harris, R. C.; Tallon, M. J.; Dunnett, M.; Boobis, L.; Coakley, J.; Kim, H. J.; Fallowfield, J. L.; Hill, C. A.; Sale, C.; Wise, J. A. The absorption of orally supplied β-alanine and its effect on muscle carnosine synthesis in human vastus lateralis. *Amino Acids* 2006, 30, 279-289). At such doses, paraesthesia becomes a significant impediment to the use of β-alanine to improve physical performance. As a result of the dosage limitations, β-alanine is typically administered at lower doses (e.g., 800 mg-1600 mg) two to four times daily for 4-6 weeks before peak effect on physical performance is observed.

SUMMARY OF THE INVENTION

The present invention is directed to compositions and methods provide the ability to administer larger doses of β-alanine and/or administer doses of β-alanine over a shorter period of time.

The present invention relates in some aspects to compositions, formulations (e.g., pharmaceutical, nutritional, etc.), and food or beverage products comprising (a) β-alanine or a derivative of β-alanine; and (b) at least one agent that modulates the N-methyl D-aspartate (NMDA) pathway. The compositions, formulations, and food or beverage products are useful for, among other things, improving tolerance and compliance to higher doses of β-alanine and reducing the time that it takes to achieve a beneficial effect (e.g., peak effect) of β-alanine.

In some aspects a composition of the present invention comprises (a) β-alanine or a derivative of β-alanine; and (b) at least one agent that modulates the N-methyl D-aspartate (NMDA) pathway.

In some embodiments of a composition of the present invention, the ratio of (a) to (b) is 1:5 to 1:15 or 1:1 to 1:80. In some embodiments of a composition of the present invention, (a) and (b) are present in admixture. In other embodiments of a composition of the present invention, (a) and (b) are chemically linked together via a bond that is broken upon administration of the composition to a human or animal in such a way that both (a) and (b) impart a therapeutic effect to the human or animal.

In some embodiments of a composition of the present invention, the one or more agents that modulates the NMDA pathway is selected from the group consisting of L-theanine, γ-aminobutyric acid (GABA), a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above.

In some embodiments of a composition of the present invention, at least one agent that modulates the NMDA pathway is an NMDA receptor antagonist. In some embodiments of a composition of the present invention, the NMDA receptor antagonist is selected from the group consisting of dextromethorphan, ketamine, histogranin, memantine, meperidine, methadone, phencyclidine, and combinations thereof.

In some aspects a formulation of the present invention comprises (a) β-alanine or a derivative of β-alanine; and (b) at least one agent that modulates the N-methyl D-aspartate (NMDA) pathway.

In some embodiments of a formulation of the present invention, the ratio of (a) to (b) is from 2:1 to 1500:1. In some embodiments of a formulation of the present invention, (a) and (b) are present in admixture. In other embodiments of a formulation of the present invention, (a) and (b) are chemically linked together via a bond that is broken upon administration of the formulation to a human or animal in such a way that both (a) and (b) impart a therapeutic effect to the human or animal.

In some embodiments of a formulation of the present invention, the one or more agents that modulates the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above.

In some embodiments of a formulation of the present invention, at least one agent that modulates the NMDA pathway is an NMDA receptor antagonist. In some embodiments of a formulation of the present invention, the NMDA receptor antagonist is selected from the group consisting of dextromethorphan, ketamine, histogranin, memantine, meperidine, methadone, phencyclidine, and combinations thereof.

In some aspects a pharmaceutical composition of the present invention comprises (a) β-alanine or a derivative of β-alanine; (b) at least one agent that modulates the N-methyl D-aspartate (NMDA) pathway; and (c) a pharmaceutically acceptable carrier, diluent, or excipient.

In some embodiments of a pharmaceutical composition of the present invention, the ratio of (a) to (b) is from 2:1 to 1500:1. In some embodiments of a pharmaceutical composition of the present invention, (a) and (b) are present in admixture. In other embodiments of a pharmaceutical composition of the present invention, (a) and (b) are chemically linked together via a bond that is broken upon administration of the pharmaceutical composition to a human or animal in such a way that both (a) and (b) impart a therapeutic effect to the human or animal.

In some embodiments, a pharmaceutical composition of the present invention further comprises one or more other pharmaceutically active agents.

In some aspects a nutritional composition of the present invention comprises (a) β-alanine or a derivative of β-alanine; (b) at least one agent that modulates the N-methyl D-aspartate (NMDA) pathway; and (c) a nutritionally acceptable carrier, diluent or excipient.

In some embodiments of a nutritional composition of the present invention, the ratio of (a) to (b) is from 2:1 to 1500:1. In some embodiments of a nutritional composition of the present invention, (a) and (b) are present in admixture. In other embodiments of a nutritional composition of the present invention, (a) and (b) are chemically linked together via a bond that is broken upon administration of the nutritional composition to a human or animal in such a way that both (a) and (b) impart a therapeutic effect to the human or animal.

In some embodiments, a nutritional composition of the present invention further comprises one or more dietary supplements selected from the group consisting of a vitamin, a mineral, an herb, a botanical, an amino acid, an enzyme, an organ tissue, a gland tissue, a concentrate, a metabolite, a constituent, an extract, and combinations thereof.

In some embodiments, a nutritional composition of the present is in the form of a powder, a drink, a food bar, a cookie, a granule, a tablet, a pill, a capsule, a softgel, a gelcap, a solution, a salve, a lotion, or a suspension.

In some aspects a food or beverage product of the present invention comprises (a) β-alanine or a derivative of β-alanine; (b) at least one agent that modulates the N-methyl D-aspartate (NMDA) pathway; and (c) one or more common food ingredients selected from the group consisting of flavors, sugars, minerals, vitamins, stabilizers, thickeners, dietary fibers, proteins, and amino acids.

In some embodiments of a food or beverage product of the present invention, (a) and (b) are present in admixture. In other embodiments of a food or beverage product of the present invention, (a) and (b) are chemically linked together via a bond that is broken upon administration of the composition to a human or animal in such a way that both (a) and (b) impart a therapeutic effect to the human or animal.

In some embodiments, the food product comprises 99% to 80% by weight of (a).

In some embodiments, the beverage product comprises 99.8% to 85% by volume of (a).

In some embodiments, a food or beverage product of the present invention comprises one or more agents selected from the group consisting of thickeners, coloring agents, bulking agents, polyols, xylitol, mannitol, maltitol, preservatives, sodium or potassium benzoate, sodium or calcium carbonate, antioxidants, ascorbic acid, carotionoids, tocopherols or polyphenols, mono-, oligo- or polysaccharides, glucose, fructose, sucrose, soyoligosaccharides, xylo-oligosaccharides, galactooligosaccharides, artificial or natural non- or low-caloric sweeteners, aspartame, acesulfame, acidifiers in the form of edible acids, citric acids, acetic acid, lactic acid, apipic acid, flavors, emulsifiers, diluents, maltodextrose, wetting agents, glycerol, stabilizers, coatings, isotonic agents, and absorption promoting or delaying agents.

In some embodiments, a food or beverage product of the present invention is selected from the group consisting of fruit or juice products, concentrates of fruit or juice products, lemonades, dairy products, frozen confectionary products, baked goods, spreads, margarine, butter, peanut butter, honey, pasta products, cereal products, ready-to-serve-dishes, frozen food, tinned food, syrups, sauces, fillings, dips, chewing gums, sherbet, spices, cooking salt, and instant drink powders.

In some aspects, the present invention provides a method of enhancing physical performance in a human or animal, such method comprising administering to the human or animal an effective amount of (a) β-alanine or a derivative of β-alanine; and an effective amount of (b) at least one agent that modulates the N-methyl D-aspartate (NMDA) pathway.

In some aspects, the present invention provides a method for reducing paraesthesia in a human or animal, such method comprising co-administering to the human or animal effective amounts of (a) β-alanine or a derivative of β-alanine, and (b) at least one agent that modulates the NMDA pathway, wherein the agent that modulates the NMDA pathway reduces paraesthesia in the human or animal.

In some embodiments, the at least one agent that modulates the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above.

In some embodiments, at least one agent that modulates the NMDA pathway is an NMDA receptor antagonist. In some embodiments, the NMDA receptor antagonist is selected from the group consisting of dextromethorphan, ketamine, histogranin, memantine, meperidine, methadone, phencyclidine, and combinations thereof.

In some embodiments, the effective amount of (a) is from 15 mg/kg bodyweight to about 250 mg/kg bodyweight per day. In some embodiments, the effective amount of (b) is about 5 mg to about 4000 mg per day.

In some embodiments, (a) and (b) are administered as a composition. In other embodiments, (a) and (b) are present in admixture. In certain embodiments, (a) and (b) are chemically linked together via a bond that is broken upon administration of the composition to a human or animal in such a way that both (a) and (b) impart a therapeutic effect to the human or animal.

In some embodiments, the composition is administered orally. In some embodiments, the composition reduces intolerable paraesthesia. In some embodiments, the composition improves tolerance and compliance to higher doses of β-alanine or a derivative of β-alanine, thereby reducing the length of time it takes to achieve peak effect of β-alanine or a derivative of β-alanine on physical performance. In some embodiments, the length of time it takes to achieve peak effect of β-alanine on physical performance is reduced by up to 85% of the supplementation time period required to achieve efficacy when β-alanine or a derivative of β-alanine is dosed at 40 mg/kg bodyweight to between four and six days.

In some aspects, the present invention comprises a composition, formulation, or food or beverage product comprising between about 3 g and 10 g of β-alanine or a derivative of β-alanine, between about 300 mg and about 1000 mg of L-theanine, between about 250 mg and about 1000 mg of acetyl L-carnitine, between about 75 mg to about 200 mg of magnesium, and between about 150 mg to 750 mg of GABA.

In some aspects, the present invention comprises a composition comprising (a) β-alanine or a derivative of β-alanine; and (b) at least one agent that modulates the N-methyl D-aspartate (NMDA) pathway or a biological pathway that converges downstream with the NMDA pathway.

In some embodiments of the composition, the ratio of (a) to (b) in the composition is 1:5 to 1:15 or 1:1 to 1:80. In some embodiments, (a) and (b) are present in the composition in admixture.

In some embodiments of the composition, (a) and (b) are chemically linked together via a bond that is broken upon administration of the composition to a human or animal in such a way that both (a) and (b) impart a therapeutic effect to the human or animal.

In some embodiments of the composition, the one or more agents that modulates the NMDA pathway or a biological pathway that converges downstream with the NMDA pathway is selected from the group consisting of L-theanine, γ-aminobutyric acid (GABA), a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above.

In some embodiments of the composition, at least one agent that modulates the NMDA pathway is an NMDA receptor antagonist. In some embodiments of the composition, the NMDA receptor antagonist is selected from the group consisting of dextromethorphan, ketamine, kynurenic acid, histogranin, memantine, meperidine, methadone, phencyclidine, and combinations thereof.

In some embodiments of the composition, the biological pathway that converges downstream with the NMDA pathway is a biological pathway that converges downstream with the NMDA pathway in sensory neurons of the dorsal root ganglia. In some embodiments of the composition, the biological pathway that converges downstream with the NMDA pathway is a G-protein-coupled receptor pathway. In some embodiments of the composition, the G-protein-coupled receptor pathway is selected from the group consisting of MrgprD and MrgprX1.

In some aspects the present invention provides a formulation comprising (a) β-alanine or a derivative of β-alanine; and (b) at least one agent that modulates the N-methyl D-aspartate (NMDA) pathway or a biological pathway that converges downstream with the NMDA pathway.

In some embodiments of the formulation, the ratio of (a) to (b) is from 2:1 to 1500:1. In some embodiments of the formulation, (a) and (b) are present in admixture. In some embodiments of the formulation, (a) and (b) are chemically linked together via a bond that is broken upon administration of the formulation to a human or animal in such a way that both (a) and (b) impart a therapeutic effect to the human or animal.

In some embodiments of the formulation, the one or more agents that modulates the NMDA pathway or a biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments of the formulation, at least one agent that modulates the NMDA pathway or the biological pathway that converges downstream with the NMDA pathway is an NMDA receptor antagonist. In some embodiments of the formulation, the NMDA receptor antagonist is selected from the group consisting of dextromethorphan, ketamine, kynurenic acid, histogranin, memantine, meperidine, methadone, phencyclidine, and combinations thereof.

In some embodiments of the formulation, the biological pathway that converges downstream with the NMDA pathway is a biological pathway that converges downstream with the NMDA pathway in sensory neurons of the dorsal root ganglia. In some embodiments of the formulation, the biological pathway that converges downstream with the NMDA pathway is a G-protein-coupled receptor pathway. In some embodiments of the formulation, the G-protein-coupled receptor pathway is selected from the group consisting of MrgprD and MrgprX1.

In some aspects, the present invention provides a pharmaceutical composition comprising (a) β-alanine or a derivative of β-alanine; (b) at least one agent that modulates the N-methyl D-aspartate (NMDA) pathway or a biological pathway that converges downstream with the NMDA pathway; and (c) a pharmaceutically acceptable carrier, diluent, or excipient.

In some embodiments of the pharmaceutical composition, the ratio of (a) to (b) is from 2:1 to 1500:1. In some embodiments of the pharmaceutical composition, (a) and (b) are present in admixture. In some embodiments of the pharmaceutical composition, (a) and (b) are chemically linked together via a bond that is broken upon administration of the pharmaceutical composition to a human or animal in such a way that both (a) and (b) impart a therapeutic effect to the human or animal.

In some embodiments, the pharmaceutical composition includes one or more other pharmaceutically active agents.

In some embodiments of the pharmaceutical composition, the one or more agents that modulates the NMDA pathway or a biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments of the pharmaceutical composition, at least one agent that modulates the NMDA pathway or the biological pathway that converges downstream with the NMDA pathway is an NMDA receptor antagonist. In some embodiments of the pharmaceutical composition, the NMDA receptor antagonist is selected from the group consisting of dextromethorphan, ketamine, kynurenic acid, histogranin, memantine, meperidine, methadone, phencyclidine, and combinations thereof.

In some embodiments of the pharmaceutical composition, the biological pathway that converges downstream with the NMDA pathway is a biological pathway that converges downstream with the NMDA pathway in sensory neurons of the dorsal root ganglia. In some embodiments of the pharmaceutical composition, the biological pathway that converges downstream with the NMDA pathway is a G-protein-coupled receptor pathway. In some embodiments of the pharmaceutical composition, the G-protein-coupled receptor pathway is selected from the group consisting of MrgprD and MrgprX1.

In some aspects the present invention provides a nutritional composition comprising (a) β-alanine or a derivative of β-alanine; (b) at least one agent that modulates the N-methyl D-aspartate (NMDA) pathway or a biological pathway that converges downstream with the NMDA pathway; and (c) a nutritionally acceptable carrier, diluent or excipient.

In some embodiments of the nutritional composition, the one or more agents that modulates the NMDA pathway or biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above.

In some embodiments of the nutritional composition, at least one agent that modulates the NMDA pathway or the biological pathway that converges downstream with the NMDA pathway is an NMDA receptor antagonist. In some embodiments of the nutritional composition, the NMDA receptor antagonist is selected from the group consisting of dextromethorphan, ketamine, kynurenic acid, histogranin, memantine, meperidine, methadone, phencyclidine, and combinations thereof.

In some embodiments of the nutritional composition, the biological pathway that converges downstream with the NMDA pathway is a biological pathway that converges downstream with the NMDA pathway in sensory neurons of the dorsal root ganglia. In some embodiments of the nutritional composition, the biological pathway that converges downstream with the NMDA pathway is a G-protein-coupled receptor pathway. In some embodiments of the nutritional composition, the G-protein-coupled receptor pathway is selected from the group consisting of MrgprD and MrgprX1.

In some embodiments of the nutritional composition, the ratio of (a) to (b) is from 2:1 to 1500:1. In some embodiments of the nutritional composition, (a) and (b) are present in admixture. In some embodiments of the nutritional composition, (a) and (b) are chemically linked together via a bond that is broken upon administration of the nutritional composition to a human or animal in such a way that both (a) and (b) impart a therapeutic effect to the human or animal. In some embodiments, the nutritional composition includes one or more dietary supplements selected from the group consisting of a vitamin, a mineral, an herb, a botanical, an amino acid, an enzyme, an organ tissue, a gland tissue, a concentrate, a metabolite, a constituent, an extract, and combinations thereof.

In some embodiments, the nutritional composition is in the form of a powder, a drink, a food bar, a cookie, a granule, a tablet, a pill, a capsule, a softgel, a gelcap, a solution, a salve, a lotion, or a suspension.

In some aspects the present invention provides a food or beverage product comprising (a) β-alanine or a derivative of β-alanine; (b) at least one agent that modulates the N-methyl D-aspartate (NMDA) pathway or a biological pathway that converges downstream with the NMDA pathway; and (c) one or more common food ingredients selected from the group consisting of flavors, sugars, minerals, vitamins, stabilizers, thickeners, dietary fibers, proteins, and amino acids.

In some embodiments of the food or beverage product, the one or more agents that modulates the NMDA pathway or biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments of the food or beverage product, at least one agent that modulates the NMDA pathway or the biological pathway that converges downstream with the NMDA pathway is an NMDA receptor antagonist. In some embodiments of the food or beverage product, the NMDA receptor antagonist is selected from the group consisting of dextromethorphan, ketamine, kynurenic acid, histogranin, memantine, meperidine, methadone, phencyclidine, and combinations thereof.

In some embodiments of the food or beverage product, the biological pathway that converges downstream with the NMDA pathway is a biological pathway that converges downstream with the NMDA pathway in sensory neurons of the dorsal root ganglia. In some embodiments of the food or beverage product, the biological pathway that converges downstream with the NMDA pathway is a G-protein-coupled receptor pathway. In some embodiments of the food or beverage product, the G-protein-coupled receptor pathway is selected from the group consisting of MrgprD and MrgprX1.

In some embodiments of the food or beverage product, (a) and (b) are present in admixture. In some embodiments of the food or beverage product, (a) and (b) are chemically linked together via a bond that is broken upon administration of the composition to a human or animal in such a way that both (a) and (b) impart a therapeutic effect to the human or animal.

In some embodiments, the food product comprises 99% to 80% by weight of (a). In some embodiments, the beverage product comprises 99.8% to 85% by volume of (a).

In some embodiments, the food or beverage product includes one or more agents selected from the group consisting of thickeners, coloring agents, bulking agents, polyols, xylitol, mannitol, maltitol, preservatives, sodium or potassium benzoate, sodium or calcium carbonate, antioxidants, ascorbic acid, carotenoids, tocopherols or polyphenols, mono-, oligo- or polysaccharides, glucose, fructose, sucrose, soyoligosaccharides, xylo-oligosaccharides, galactooligosaccharides, artificial or natural non- or low-caloric sweeteners, aspartame, acesulfame potassium, sucralose, acidifiers in the form of edible acids, citric acids, acetic acid, lactic acid, apipic acid, flavors, emulsifiers, diluents, maltodextrose, wetting agents, glycerol, stabilizers, coatings, isotonic agents, and absorption promoting or delaying agents.

In some embodiments, the food or beverage product is selected from the group consisting of fruit or juice products, concentrates of fruit or juice products, lemonades, dairy products, frozen confectionary products, baked goods, spreads, margarine, butter, peanut butter, honey, pasta products, cereal products, ready-to-serve-dishes, frozen food, tinned food, syrups, sauces, fillings, dips, chewing gums, sherbet, spices, cooking salt, and instant drink powders.

In some aspects the present invention provides a method of enhancing physical performance in a human or animal comprising administering to the human or animal an effective amount of (a) β-alanine or a derivative of β-alanine; and an effective amount of (b) at least one agent that modulates the N-methyl D-aspartate (NMDA) pathway or a biological pathway that converges downstream with the NMDA pathway.

In some embodiments of the method, at least one agent that modulates the NMDA pathway or biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments of the method, at least one agent that modulates the NMDA pathway or biological pathway that converges downstream with the NMDA pathway is an NMDA receptor antagonist. In some embodiments of the method, the NMDA receptor antagonist is selected from the group consisting of dextromethorphan, ketamine, histogranin, memantine, meperidine, methadone, phencyclidine, and combinations thereof.

In some embodiments of the method, the biological pathway that converges downstream with the NMDA pathway is a biological pathway that converges downstream with the NMDA pathway in sensory neurons of the dorsal root ganglia. In some embodiments of the method, the biological pathway that converges downstream with the NMDA pathway is a G-protein-coupled receptor pathway. In some embodiments of the method, the G-protein-coupled receptor pathway is selected from the group consisting of MrgprD and MrgprX1.

In some embodiments of the method, the effective amount of (a) is from 15 mg/kg bodyweight to about 250 mg/kg bodyweight per day. In some embodiments of the method, the effective amount of (b) is about 5 mg to about 4000 mg per day. In some embodiments of the method, (a) and (b) are administered as a composition.

In some embodiments of the method, (a) and (b) are present in the composition admixture. In some embodiments of the method, (a) and (b) are chemically linked together in the composition via a bond that is broken upon administration of the composition to a human or animal in such a way that both (a) and (b) impart a therapeutic effect to the human or animal.

In some embodiments of the method, the composition is administered orally.

In some embodiments, the composition reduces intolerable paraesthesia. In some embodiments, the composition reduces a sensation of discomfort selected from the group consisting of burning, flushing, itching, pins and needles, tingling, and combinations thereof, due to (a) in the composition. In some embodiments, the composition improves tolerance and compliance to higher doses of β-alanine or a derivative of β-alanine, thereby reducing the length of time it takes to achieve peak effect of β-alanine or a derivative of β-alanine on physical performance. In some embodiments, the length of time it takes to achieve peak effect of β-alanine on physical performance is reduced by between 10% to 85% of the supplementation time period required to achieve efficacy when β-alanine or a derivative of β-alanine is dosed at 40 mg/kg bodyweight to between four and 21 days.

In some aspects the present invention provides a method for reducing paraesthesia in a human or animal, the method comprising co-administering to the human or animal effective amounts of (a) β-alanine or a derivative of β-alanine, and (b) at least one agent that modulates the NMDA pathway or a biological pathway that converges downstream with the NMDA pathway, wherein the agent that modulates the NMDA pathway or the biological pathway that converges downstream with the NMDA pathway reduces paraesthesia in the human or animal.

In some embodiments of the method, the paraesthesia is selected from the group consisting of burning, flushing, itching, pins and needles, tingling, and combinations thereof. In some embodiments of the method, the at least one agent that inhibits the NMDA pathway or biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments of the method, at least one agent that inhibits the NMDA pathway or biological pathway that converges downstream with the NMDA pathway is an NMDA receptor antagonist. In some embodiments of the method, the NMDA receptor antagonist is selected from the group consisting of dextromethorphan, kynurenic acid, ketamine, histogranin, memantine, meperidine, methadone, phencyclidine, and combinations thereof.

In some embodiments of the method, the biological pathway that converges downstream with the NMDA pathway is a biological pathway that converges downstream with the NMDA pathway in sensory neurons of the dorsal root ganglia. In some embodiments of the method, the biological pathway that converges downstream with the NMDA pathway is a G-protein-coupled receptor pathway. In some embodiments of the method, the G-protein-coupled receptor pathway is selected from the group consisting of MrgprD and MrgprX1.

In some embodiments of the method, the effective amount of (a) is from about 15 mg/kg bodyweight to about 250 mg/kg bodyweight per day. In some embodiments of the method, the effective amount of (b) is about 5 mg to about 4000 mg per day. In some embodiments, (a) and (b) are administered as a composition. In some embodiments, (a) and (b) are present in admixture. In some embodiments, (a) and (b) are chemically linked together via a bond that is broken upon administration of the composition to a human or animal in such a way that both (a) and (b) impart a therapeutic effect to the human or animal. In some embodiments, the composition is administered orally. In some embodiments, the composition improves tolerance and compliance to higher doses of β-alanine or a derivative of β-alanine, thereby reducing the length of time it takes to achieve peak effect on physical performance. In some embodiments, the length of time it takes to achieve peak effect of β-alanine on physical performance is reduced by up to 85% of the supplementation time period required to achieve efficacy when β-alanine or the derivative of β-alanine is dosed at 40 mg/kg bodyweight to between four and six days.

In some aspects the present invention provides a composition, formulation, or food or beverage product comprising (a) between about 3 g and 10 g of β-alanine or a derivative of β-alanine, and (b) one or more of between about 300 mg and about 1000 mg of L-theanine, between about 250 mg and about 1000 mg of acetyl L-carnitine, between about 75 mg to about 200 mg of magnesium, and between about 150 mg to 750 mg of GABA.

In some aspects the present invention provides a composition, formulation, or food or beverage product comprising (a) about 3 g to about 10 g of β-alanine or a derivative of β-alanine, and (b) about 100 mg to about 1000 mg of L-theanine.

In some aspects the present invention provides a composition, formulation, or food or beverage product comprising (a) about 3 g to about 10 g of β-alanine or a derivative of β-alanine, (b) about 100 mg to about 1000 mg of L-theanine, and (c) about 100 mg to 500 mg of wild *jujube* seed extract.

In some aspects the present invention provides a method of improving tolerability to β-alanine in a human or animal, the method comprising administering a composition comprising (a) β-alanine or a derivative of β-alanine; and (b) at least one agent that modulates the N-methyl D-aspartate (NMDA) pathway or a biological pathway that converges downstream with the NMDA pathway.

In some embodiments, the at least one agent that modulates the NMDA pathway or biological pathway that converges downstream with the NMDA pathway is selected from the group consisting of L-theanine, GABA, a GABA precursor, magnesium, L-carnitine, L-glycine, agamatine, botanical rhizome preparations or extracts selected from the group consisting of Acorus gramineus, *Polygala* tenuifolia, *Celastrus paniculatus*, and, *Zizyphus jujuba* var. *spinosa* (Zizyphi Spinosa Semen), and combinations of any of the above. In some embodiments, at least one agent that modulates the NMDA pathway or biological pathway that converges downstream with the NMDA pathway is an NMDA receptor antagonist. In some embodiments, the NMDA receptor antagonist is selected from the group consisting of dextromethorphan, ketamine, histogranin, memantine, meperidine, methadone, phencyclidine, and combinations thereof.

In some embodiments, the biological pathway that converges downstream with the NMDA pathway is a biological pathway that converges downstream with the NMDA pathway in sensory neurons of the dorsal root ganglia. In some embodiments, the biological pathway that converges downstream with the NMDA pathway is a G-protein-coupled receptor pathway. In some embodiments, the G-protein-coupled receptor pathway is selected from the group consisting of MrgprD and MrgprX1.

DETAILED DESCRIPTION OF THE INVENTION

Figure 1:
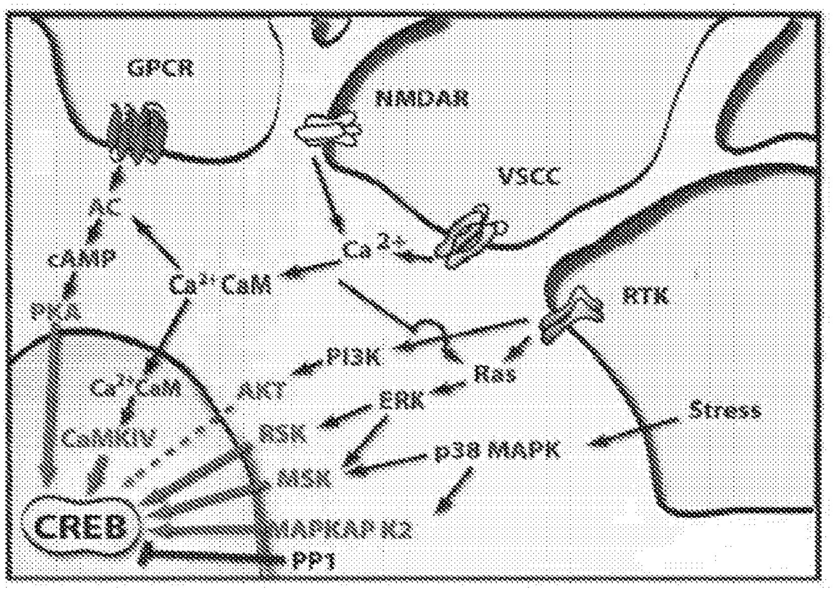
FIG. 1 is a schematic representation of biological pathways that converge downstream with the NMDA pathway.

Aspects of the present invention generally relate to compositions and methods for improving the tolerability, pharmacodynamics, and efficacy of β-alanine, for example, by reducing discomfort due to parasthesia (e.g., sensations of burning, itching, flushing, pins and needles, and/or tingling, etc.) associated with administration of β-alanine alone. The improvements derive generally from the ability to administer larger doses of β-alanine and/or administer doses of β-alanine over a shorter period of time.

In some aspects the present invention relates to compositions (e.g., nutritional compositions, pharmaceutical compositions, etc.), formulations, and food or beverage products (e.g., a functional food, medical food or functional beverage) comprising, consisting essentially of, or consisting of (a) β-alanine and/or a derivative of β-alanine, and (b) at least one agent that modulates the N-methyl D-aspartate (NMDA) pathway.

In some aspects the present invention relates to compositions (e.g., nutritional compositions, pharmaceutical compositions, etc.), formulations, and food or beverage products (e.g., a functional food, medical food or functional beverage) comprising, consisting essentially of, or consisting of (a) β-alanine and/or a derivative of β-alanine, and (b) at least one agent that modulates the N-methyl D-aspartate (NMDA) pathway or a biological pathway that converges downstream with the NMDA pathway.

An exemplary composition, formulation, or food or beverage product comprises β-alanine and L-theanine (e.g., in admixture). Another exemplary composition, formulation, or food or beverage product comprises β-alanine, *Ziziphus jujube* car. *Spinosa* extract, and L-theanine (e.g., in admixture).

As used herein, the term “active agents” refers to any of the compounds disclosed herein as component (a) and/or component (b). It is also to be understood that the “active agents” comprising component (a) and component (b) may be chemically linked together, for example via a covalent bond (e.g., in the form of a dipeptide comprising (a) and (b), e.g., β-alanyl-L-theanine) or an ionic bond (e.g., in the form of a salt comprising (a) and (b), e.g., β-alanine-L-theanate) that is broken upon administration of the composition, formulation, or food or beverage product to a human or animal in such a way that both (a) and (b) impart a therapeutic effect to the human or animal.

The compositions, formulations, and food or beverage products of the present invention are useful for enhancing physical performance in a human or animal and confer advantages over administering β-alanine alone. For example, the compositions, formulations, and food or beverage products of the present invention are useful for reducing the paraesthesia associated with administration of β-alanine alone (e.g., to a tolerable level). Specifically, the compositions, formulations, and food or beverage products of the present invention permit administration of a dose of β-alanine without eliciting the moderate-to-severe paraesthesia (e.g., intolerable paraesthesia) induced by a corresponding dose of β-alanine administered alone or by other art-accepted methods. Accordingly, the compositions, formulations, and food or beverage products of the present invention improve tolerance and compliance to higher doses of β-alanine (or a derivative of β-alanine) thereby permitting administration of higher doses of β-alanine when compared to β-alanine administered alone or by other art-accepted methods and formulations.

For example, surprisingly and unexpectedly, the compositions, formulations, and food or beverage products of the present invention can provide as much as about 15 grams of β-alanine in a single dose, and as many as three single 15 gram doses of β-alanine can be consumed daily without eliciting intolerable paraesthesia. Preferably, the compositions, formulations, and food or beverage products of the present invention provide between about 6 to 10 grams of β-alanine in a single dose that can be consumed as much as three times daily. When consumed in this manner, the compositions, formulations, and food or beverage products of the present invention surprisingly and unexpectedly improve tolerance and compliance to higher doses of β-alanine, thereby reducing the length of time required to achieve effect (e.g., peak effect) of β-alanine on physical performance by up to 85% (e.g., from about 4-6 weeks to about 4-6 days) of the supplementation time period required to achieve efficacy when β-alanine is dosed at 40 mg/kg bodyweight in a human or animal. In some embodiments, the compositions, formulations, and food or beverage products of the present invention reduce the length of time require to achieve effect (e.g., peak effect) of β-alanine on physical performance by between 10% to 85% (e.g., from about 4-6 weeks to about 4-21 days) of the supplementation time period required to achieve efficacy when β-alanine is dosed at 40 mg/kg bodyweight in a human or animal.

The compositions, formulations, and food or beverage products of the present invention can provide improved nutritional and/or therapeutic efficacy as compared to their individual effects.

The invention also relates to administration of the composition, formulation, or food or beverage product to a human or animal in a method for enhancing physical performance/function in the human or animal and/or in a method for reducing intolerable β-alanine-induced paraesthesia in the human or animal to a tolerable level. It is to be understood that reduction of intolerable β-alanine-induced paraesthesia to a tolerable level can be objectively quantified as a change in an individual's anchored 100 mm VAS score, on a scale from 0-100 mm, from 60 mm-90 mm (when ingesting β-alanine alone) to about a 10 mm-30 mm (when ingesting β-alanine and at least one agent that modulates the NMDA pathway).

As used herein, "physical performance/function" refers to any physical attribute dependent on contraction of skeletal muscle. For example, physical function/performance includes, but is not limited to, optimal muscular strength, muscular endurance, running speed and endurance, swimming speed and endurance, throwing power, lifting and pulling power.

β-Alanine

β-alanine (e.g., in substantially pure form, or modified to improve a property of β-alanine such as shelf-life, half-life, stability, bioavailability, etc.) is an active agent of the present invention. As used herein, the invention also encompasses one or more compounds (e.g., isolated or synthetic) other than β-alanine that increase endogenous levels of β-alanine in a human or animal when administered to the human or animal, such as carnosine, balenine, and anserine, for example. β-alanine (CAS Registry No. 107-95-9, sometimes known as 2-Carboxyethylamine or 3-Aminopropanoic acid) is a naturally occurring beta amino acid, has a molecular weight of about 89.0933, and has the structure below.

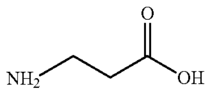

β-Alanine

β-alanine is widely used as a dietary supplement for, inter alia, increasing muscle carnosine concentration, decreasing fatigue in athletes, reducing muscle fatigue, reducing muscle damage, promoting endurance, promoting recovery, increasing strength, and improving overall physical performance and body composition. These benefits of β-alanine are well-documented and usually increase with dose. However, oral administration of β-alanine at doses greater than 10 mg/kg body weight can result in sensory paraesthesia. The paraesthesia is often described as being akin to a flushing vasomotor phenomenon with burning, itching, and superficial skin discomfort that may involve the head and neck, arms, back and proximal lower extremities. It can also be described as being similar to the vasomotor symptoms associated with nicotinic acid (niacin) ingestion. In some embodiments, paraesthesia is described as a subjective sensation of overall discomfort selected from the group consisting of burning, flushing, itching, pins and needles, tingling, and combinations thereof. Paraesthesia is relatively mild at about 10 mg/kg, and oral doses of 40 mg/kg or higher can result in moderate-to-severe paraesthesia. As a result of these dosage limitations, β-alanine is typically administered at lower doses, multiple times per day, for about 4-6 weeks before peak effect on physical performance is observed. In some instances, paraesthesia can be so intolerable that some individuals may choose to avoid β-alanine supplementation entirely.

During the course of work described herein, it was surprisingly and unexpectedly found that the paraesthesia elicited by β-alanine can be reduced (e.g., to a tolerable level) by co-administering to a human or animal (a) β-alanine and/or a derivative of β-alanine, and (b) at least one modulator of the N-methyl D-aspartate (NMDA) pathway or a pathway which converges downstream with the NMDA pathway. Moreover, surprisingly and unexpectedly, co-administering (a) and (b) to the human or animal allows the human or animal to consume as much as 15 grams of β-alanine in a single dose and to take as many as three 15 gram doses of β-alanine per day without eliciting intolerable paraesthesia.

Preferably, the compositions, formulations, and food or beverage products of the present invention provide between about 6 to 10 grams of β-alanine in a single dose, and allow as many of three such 6 to 10 gram single doses of β-alanine to be consumed per day. When consumed in this manner, peak effect of β-alanine on physical performance can be achieved in as little as 4-6 days of administration, typically without eliciting intolerable paraesthesia. In some embodiments, peak effect of β-alanine on physical performance can be achieved in as little as 4-21 days of administration, typically without eliciting intolerable paraesthesia. Stated differently, co-administering (a) and (b) achieves a peak effect of β-alanine on physical performance in as little as between approximately 10% to 15% of the time it takes to elicit peak effect when β-alanine is administered in a conventional manner, and increases the extent or magnitude of effect as a result of increasing intramuscular carnosine concentration, which has been deemed to be related to total beta-Alanine dose consumed over the supplementation period.

Accordingly, the compositions, formulations, and food or beverage products of the present invention improve tolerance and compliance to higher doses of β-alanine, thereby permitting usage of higher doses of β-alanine when compared to β-alanine administered alone or in art-recognized formulations or compositions. In some instances, depending on the actual dosage of β-alanine consumed by a human or animal, paraesthesia in the human or animal may be prevented or reduced entirely.

The objective of the present invention, however, is to reduce intolerable paraesthesia to a tolerable level so that the human or animal can consume higher doses of β-alanine to reduce the length of time it takes to achieve peak effect, and increase the magnitude or extent of the effect of β-alanine on physical performance, and to do so in a way that the individual or animal can still feel that the β-alanine is working. Without wishing to be bound by theory, it is believed that complete prevention or reduction of β-alanine-induced paraesthesia in a human or animal could cause the human or animal to feel that the β-alanine-is not working properly, which could also interfere with compliance.

Of course, it should be appreciated that the present invention contemplates the usage of any dosage of β-alanine that may be commercially desirable. For example, a single dose of β-alanine in a composition, formulation, or food or beverage product of the present invention can be about 1.6 grams, and such dose can be consumed several times per day or per administration or more. In some instances, a composition, formulation, or food or beverage product of the present invention provides β-alanine in a single dose of 3.2 grams, and such dose can be consumed several times per day or more.

Derivatives of β-Alanine

A derivative of β-alanine can be used as an active agent of the present invention. As used herein, "derivative of β-alanine" refers to a compound that, when delivered to the human or animal body, imparts the same or similar physiological effects as β-alanine on muscle and other tissues.

An exemplary derivative of β-alanine that can be used as an active agent in the compositions, formulations, and food or beverage products of the present invention is N-acetyl-β-alanine (CAS Registry No. 3025-95-4).

Other exemplary derivatives of β-alanine that can be used as active agents in the compositions, formulations, and food or beverage products of the present invention include the fluorinated methyl β-alanine derivatives, for example 3-amino-3-fluoromethylpropionic acid, disclosed in U.S. Pat. No. 4,375,477, incorporated herein by reference in its entirety.

Additional exemplary derivatives of β-alanine that can be used as active agents in the compositions, formulations, and food or beverage products of the present invention also include β-alanine esters or amides, for example the carboxylic acid salts of β-alanine esters or amides disclosed in European Patent Publication No. EP1734034, incorporated herein by reference in its entirety.

Other exemplary derivatives of β-alanine that can be used as active agents in the compositions, formulations, and food or beverage products of the present invention include salts of β-alanine, for example organic salts of β-alanine disclosed in U.S. Pat. No. 7,956,218, incorporated herein by reference in its entirety.

Another exemplary derivative of β-alanine that can be used as an active agent in the compositions, formulations, and food or beverage products of the present invention is β-alanine nitrate.

Derivatives of β-alanine that can be used as active agents in the compositions, formulations, and food or beverage products of the present invention are not intended to be limited to the specifically mentioned derivatives, and other derivatives will be apparent to those skilled in the art.

Agent that Modulates the NMDA Pathway

As used herein, "NMDA pathway" refers to the biological pathway and associated physiological effects triggered by direct or indirect modulation of the N-methyl D-aspartate (NMDA) receptor. The NMDA receptor is a subclass of glutamate receptors; glutamate is an excitatory neurotransmitter of the mammalian central nervous system. The NMDA receptor plays a role in synaptic plasticity underlying cognitive functions, for example memory and learning, and in nociceptive pathways.

The present invention contemplates the use of any agent that modulates (partially or completely) NMDA pathway activity regardless of its chemical composition or mechanism of action, including agents that modulate a biological pathway that converges downstream with the NMDA pathway. Stated differently, the term "NMDA pathway" encompasses any biological pathway that converges downstream with the NMDA pathway. FIG. 1 is a schematic representation of signaling pathways that converge downstream on transcription factor CREB (see, e.g., Lonze and Ginty, "Function and regulation of CREB family transcription factors in the nervous system", *Neuron.* 2002; 35(4):605-23), which is incorporated herein by reference). As is shown in FIG. 1, one example of a biological pathway that converges downstream with the NMDA pathway is the G-protein coupled receptor (GPCR) pathway. The Mrgpr family of GPCR receptors expressed in neurons (e.g., sensory neurons in the dorsal root ganglia) have been reported to be involved in eliciting skin paresthesia (e.g., itch and tingling) in humans (see, e.g., Liu, et al., "Mechanisms of itch evoked by β-alanine," *J Neurosci.* 2012; 32(42):14532-14537; and Shinohara, et al., "Identification of a G Protein-coupled Receptor Specifically Responsive to β-alanine," *J Biol Chem.* 2004; 279(22):23559-23564, both of which are incorporated herein by reference). Accordingly, without wishing to be bound by theory, it is believed that the Mrgpr family of GPCR receptors are a biological pathway that converges downstream with the NMDA pathway, e.g., in sensory neurons of the dorsal root ganglia. Exemplary such Mrgpr receptors include, but are not limited to, the MrgprD receptor and the MrgprX1 receptor. Other biological pathways that converge downstream with the NMDA pathway are depicted in FIG. 1.

L-Theanine

An exemplary agent that modulates the NMDA pathway that can be used as an active agent in the compositions, formulations, and food or beverage products of the present invention is L-theanine. L-theanine is typically used with the intention of increasing sense of calm and relaxation, without interfering with other aspects of cognitive function such as concentration and attention. There is no known public record of L-theanine being considered in combination with β-alanine to improve the functional characteristics of β-alanine or to improve tolerance and compliance with β-alanine consumption.

L-theanine (CAS Registry No. 3081-61-6, also referred to as N-ethyl-L-glutamine or L-glutamic acid-γ-monoethylamide) is a glutamic acid derivative present in tea leaves, has a molecular weight of about 174.20, and has the structure shown below.

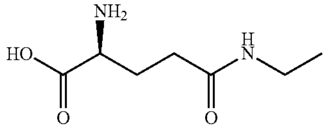

L-Theanine

L-theanine can be used as an active agent in the compositions, formulations, and food or beverage products of the present invention in any form (e.g., purified, crudely purified, extract, etc.), derived from any source (e.g., a commercial supplier), and prepared in any manner. For example, L-theanine can be produced using methods of organic synthesis (See, e.g., *Chem. Pharm. Bull.,* 19(7), 1301-1307 (1971); fermentation (Japanese Patent Laid-Open Nos. Hei 5-68578 and Hei 5-328986); or modification methods thereof using an ethylamine derivative, such as ethylamine hydrochloride, in place of ethylamine; a method comprising reacting pyroglutamic acid with ethylamine hydrochloride (Japanese Patent Laid-Open No. Hei 9-263573); a plant cell culture method (Japanese Patent Laid-Open No. Hei 5-123166); and a method using extraction from tea-leaves, with preference given to the fermentation methods, which achieve large amounts of L-theanine at low costs. The teachings of all of these references are incorporated herein by reference in their entirety. The term "tea-leaves" as used herein refers to leaves obtained from any tea plant that contains desirable amounts of L-theanine (e.g., green tea, oolong tea, black tea, and the like).

The present invention contemplates administering any amount of L-theanine that is effective at modulating the NMDA pathway or otherwise reducing intolerable β-alanine-induced paraesthesia to a tolerable level. It will be apparent to those skilled in the art that the actual amount of L-theanine to be administered in combination with β-alanine or a derivative of β-alanine can vary. For example, an effective concentration of L-theanine can be a ratio of L-theanine:β-alanine ranging from about 1:5 to about 1:15. A particularly effective concentration of L-theanine can be a ratio of L-theanine: β-alanine ranging from about 1:6 to 1:8. Exemplary dosages of L-theanine can range from about 300 mg of L-theanine when used with 40 mg/kg of β-alanine in an 80 kg human subject to up to about 1200 mg of L-theanine when using doses of up to 90 mg/kg of β-alanine in an 80 kg human subject.

γ-aminobutyric Acid (GABA)

An additional exemplary agent that modulates the NMDA pathway that can be used as an active agent in the compositions, formulations, and food or beverage products of the present invention is GABA.

GABA (CAS Registry No. 56-12-2, also referred to as 4-aminobutanoic acid) is a major inhibitory transmitter, has a molecular weight of about 103.12, and has the structure below.

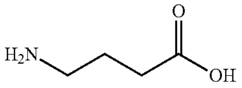

GABA

The present invention contemplates the use of any form or source of GABA that is capable of modulating the NMDA pathway in a human or animal (e.g., GABA, a GABA analog, a GABA derivative, a GABA precursor, or GABA prodrug).

The present invention contemplates administering any amount of GABA that is effective at modulating the NMDA pathway or otherwise reducing intolerable β-alanine-induced paraesthesia to a tolerable level. It will be apparent to those skilled in the art that the actual amount of GABA to be administered may vary. Exemplary dosages of GABA to be employed in the compositions, formulations, and food or beverage products of the present invention range from about 200 mg to about 800 mg, up to three times per day.

Examples of suitable GABA analogs include, but are not limited to gabapentin, pregabalin, vigabatrin, and baclofen. Examples of additional GABA analogs that can be used as active agents in the compositions, formulations, and food or beverage products of the present invention are disclosed in PCT International Publication Nos. WO 92/09560; WO 93/23383; WO 97/29101; WO 97/33858; WO 97/33859; WO 98/17627; WO 99/08671; WO 99/21824; WO 99/31057; WO 99/31074; WO 99/31075; WO 99/61424; WO 00/15611; WO 00/31020; WO 00/50027; and WO 02/00209, all of which are incorporated herein by reference in their entirety.

Alternatively, a GABA derivative can be used as an active agent in the compositions, formulations, and food or beverage products of the present invention as the at least one agent that modulates the NMDA pathway. An exemplary GABA derivative is phenibut (CAS Registry No. 1078-21-3, also known as (RS)-4-amino-3-phenyl-butryic acid, beta-phenyl-γ-aminobutryic acid, phenylGABA, fenibut, or phenybut).

Other GABA derivatives and analogs that can be used as active agents in the compositions, formulations, and food or beverage products of the present invention will be apparent to those skilled in the art.

GABA Precursors

A GABA precursor can also be used as an active agent in the compositions, formulations, and food or beverage products of the present invention. The present invention contemplates the use of any GABA precursor that is capable of increasing endogenous levels of GABA in a human or animal upon administration to the human or animal.

Exemplary GABA precursors for use as active agents in the compositions, formulations, and food or beverage products of the present invention include, inter alia, glutamate and pyridoxal phosphate (e.g., pyridoxal-5-phosphate).

Exemplary dosages of pyridoxal phosphate to be employed in the compositions, formulations, and food or beverage products of the present invention range from about 1 mg to about 100 mg.

Exemplary dosages of glutamate to be employed in the compositions, formulations, and food or beverage products of the present invention range from about 100 mg to about 4 grams.

A GABA precursor for use as an active agent in the compositions, formulations, and food or beverage products of the present invention can also be a prodrug that is capable of being metabolized in the human or animal body to GABA. For example, the prodrug Picamilon, which crosses the blood-brain barrier and is hydrolyzed into GABA and niacin, can be a suitable GABA precursor.

Magnesium

An additional exemplary agent that modulates the NMDA pathway that can be used as an active agent in the compositions, formulations, and food or beverage products of the present invention is magnesium.

Magnesium (CAS Registry No. 7439-95-4, referred to by the symbol Mg) is an abundant alkaline earth metal having an atomic number of 12. The present invention contemplates the use of any form of magnesium that is capable of modulating the NMDA pathway in the human or animal body. For example, a magnesium salt can be used as an active agent in the compositions, formulations, and food or beverage products of the present invention as the at least one agent that modulates the NMDA pathway.

Exemplary magnesium salts useful as active agents of the present invention include, but are not limited to magnesium hydroxide, magnesium chloride, magnesium oxide, magnesium gluconate, magnesium malate, magnesium orotate, magnesium glycinate, and magnesium citrate, magnesium bromide. Other suitable magnesium salts will be apparent to those skilled in the art.

The present invention contemplates administering any amount of magnesium that is effective at modulating the NMDA pathway or otherwise reducing intolerable β-alanine-induced paraesthesia to a tolerable level. It will be apparent to those skilled in the art that the actual amount of magnesium to be administered may vary. Exemplary dosages of magnesium to be employed in the compositions, formulations, and food or beverage products of the present invention can range from about 100 mg to about 350 mg.

L-Carnitine

An additional exemplary agent that modulates the NMDA pathway that can be used as an active agent in the compositions, formulations, and food or beverage products of the present invention is L-carnitine or a salt or derivative of L-carnitine.

The present invention contemplates the use of any form of L-carnitine that is capable of modulating the NMDA pathway in a human or animal body (e.g., acetyl L-carnitine, acetyl L-carnitine derivatives, acetyl L-carnitine analogs, acetyl L-carnitine precursors), by enhancing the reuptake of glutamate and aspartate, thus preventing glutamate and aspartate binding to and activation of NMDA receptors.

For example, L-carnitine can be administered as acetyl-L-carnitine, propionyl-L-carnitine, L-carnitine L-tartate, L-carnitine fumarate, aminocarnitines (e.g., GPLC and APLC).

Further exemplary forms of L-carnitine that can be used as active agents in the present invention include salts of L-carnitine disclosed in U.S. Pat. No. 6,703,042 (incorporated herein by reference in its entirety), including acetyl L-carnitine L-isoleucinate hydrochloride, acetyl L-carnitine L-cysteinate hydrochloride, acetyl L-carnitine L-arginate dihydrochloride, acetyl L-carnitine L-glutamninate hydrochloride, acetyl L-carnitine L-asparaginate hydrochloride, acetyl L-carnitine glycinate hydrochloride, acetyl L-carnitine L-alaninate hydrochloride, acetyl L-carnitine L-threoninate hydrochloride, acetyl L-carnitine L-serinate hydrochloride, and acetyl L-carnitine L-typtophanate hydrochloride.

The present invention contemplates administering any amount of L-carnitine that is effective at modulating the NMDA pathway or otherwise reducing intolerable β-alanine-induced paraesthesia to a tolerable level. It will be apparent to those skilled in the art that the actual amount of L-carnitine to be administered may vary. Exemplary dosages of L-carnitine to be employed in the compositions, formulations, and food or beverage products of the present invention can range from about 150 mg to about 3000 mg.

L-Glycine

An additional exemplary agent that modulates the NMDA pathway that can be used as an active agent in the compositions, formulations, and food or beverage products of the present invention is L-glycine or a salt or derivative of L-glycine.

The present invention contemplates the use of any form of L-glycine that is capable of modulating the NMDA pathway in a human or animal body.

The present invention contemplates administering any amount of L-glycine that is effective at modulating the NMDA pathway or otherwise reducing intolerable β-alanine-induced paraesthesia. It will be apparent to those skilled in the art that the actual amount of L-glycine to be administered may vary. Exemplary dosages of L-glycine to be employed in the compositions, formulations, and food or beverage products of the present invention can range from about 10 mg to about 4000 mg per day.

Polyamine Aryliminoguanidine Derivatives

Polyamine aryliminoguanidine derivatives (e.g., agamatine) are additional exemplary agents that modulate the NMDA pathway and can be used as active agents in the compositions, formulations, and food or beverage products of the present invention.

The present invention contemplates the use of any polyamine aryliminoguanidine derivative that is capable of modulating the NMDA pathway in a human or animal body.

The present invention contemplates administering any amount of polyamine aryliminoguanidine derivative that is effective at modulating the NMDA pathway or otherwise reducing intolerable β-alanine-induced paraesthesia to a tolerable level. It will be apparent to those skilled in the art that the actual amount of polyamine aryliminoguanidine derivative to be administered may vary. Exemplary dosages of agamatine to be employed in the compositions, formulations, and food or beverage products of the present invention can range from about 10 mg to about 3000 mg per day.

Botanical Preparations or Extracts of Rhizomes

Botanical preparations or extracts of rhizomes are additional exemplary agents that modulate the NMDA pathway and can be used as active agents in the compositions, formulations, and food or beverage products of the present invention.

The present invention contemplates the use of any botanical rhizome preparation or extract that is capable of modulating the NMDA pathway in a human or animal body. Exemplary botanical preparations or extracts of rhizomes include, but are not limited to, Acorus gramineus, *Polygala* tenuifolia, *Celastrus paniculatus*, and *Zizyphus jujuba* var. *spinosa* (Zizyphi Spinosa Semen), also known as wild *jujube* seed extract).

The present invention contemplates administering any amount of botanical rhizome preparation or extract that is effective at modulating the NMDA pathway or otherwise reducing intolerable β-alanine-induced paraesthesia to a tolerable level. It will be apparent to those skilled in the art that the actual amount of botanical rhizome preparation or extract to be administered may vary. Exemplary dosages of botanical rhizome preparation or extract to be employed in the compositions, formulations, and food or beverage products of the present invention can range from about 40 mg to about 5000 mg per day.

NMDA Receptor Antagonist

Additional exemplary agents that modulate the NMDA pathway and are useful as an active agent in the compositions, formulations and food or beverage products of the present invention are NMDA receptor antagonists. As used herein, "NMDA receptor antagonist" refers to an agent that blocks or suppresses the activity of the NMDA receptor pathway regardless of its chemical form or mechanism of action. The present invention contemplates the use of any NMDA receptor antagonist that is capable of modulating the NMDA pathway. Exemplary NMDA receptor antagonists for use as active agents in the compositions, formulations, and food or beverage products of the present invention include, but are not limited to, dextromethorphan or an analog or derivative thereof, histogranin or an analog or derivative thereof, ketamine or an analog or derivative thereof, memantine or an analog or derivative thereof, meperidine or an analog or derivative thereof, methadone or an analog or derivative thereof, and phencyclidine or an analog or derivative thereof. Another exemplary NMDA receptor antagonist is kynurenic acid (a metabolite of L-tryptophan).

Other NMDA receptor antagonists suitable for use as active agents in the compositions, formulations, and food or beverage products of the present invention will be apparent to those skilled in the art (e.g., anti-receptor antibodies, anti-ligand antibodies, etc.).

The compositions, formulations, and food or beverage products of the present invention can be administered together with (separately, in rapid succession, or at intervals) additional optional agents (e.g., active agents).

Additional optional active agents can be selected from: one or more carbohydrates (e.g., amylose, fructose, glucose, isomaltulose, lactose, ribose, sucrose, trehalose, maltodextrin, etc.); one or more vitamins (e.g., water soluble vitamins, e.g., Vitamins C, B1, B2, B3, B5, B6, B12, and/or K, or lipid soluble vitamin, e.g., Vitamins A, D, E, etc.); one or more minerals (e.g., calcium, chromium, copper, iron, potassium, sodium, vanadium, and/or zinc, etc.); one or more amino acids or derivatives thereof (e.g., glycine, L-alanine, L-arginine, L-aspartic acid, D-aspartic acid, N-methyl-D-aspartic acid, L-cystine, L-glutamic acid, L-glutamine, L-histidine, L-isoleucine, L-leucine, L-lysine, L-methionine, L-ornithine, L-phenylalanine, L-ornathine, L-proline, L-serine, taurine, L-threonine, L-tryptophan, L-tyrosine, and/or L-valine and derivatives of any of these.); creatine or a salt, ester, chelate, amide, or ether of creatine (e.g., creatine monohydrate, creatine ethyl ester, etc.); one or more enzymes, herbs, botanicals, concentrates, metabolites, extracts, and any combination thereof.

An exemplary additional optional active agent is a pharmaceutically active agent. Exemplary pharmaceutically active agents include, but are not limited to salicylates (e.g., aspirin), insulin, anabolic agents (e.g., IGF-I, IGF-II, testosterone, androgen analogs, pharmaceutical or naturally occurring selective androgen receptor modulators (SARMs)), myostatin inhibiting agents (e.g., follistatin preparations), cytokines having an effect on body composition (e.g., Interleukin-15) sympathomimetic agents (e.g., amphetamine-like agents, e.g. phentermine, bicarbonate solution, buffering agents (e.g., Bismuth containing solution), or any agent (pharmacological or dietary ingredient) that decreases indigestion, GI discomfort, nausea, or heartburn, for example, ginger extract or preparations, deglycyrrhizinated licorice, fennel (*Foeniculum vulgare*), aloe vera preparation (*Aloe barbadensis*), coriander, Chamomile (*Matricaria recutita*), Peppermint (*Mentha piperita*) and Anise seed (*Pimpinella anisum*).

It will be apparent to those skilled in the art which specific additional optional active agents may be beneficially included in the compositions, formulations, and food or beverage products of the present invention. It will also be apparent to those skilled in the art that the additional optional active agents can be combined in any manner with as many or as few additional optional active agents desired, depending on the particular application.

Preparations and Use

Generally, a composition, formulation, or food or beverage product of the present invention is prepared by combining appropriate concentrations of (a) β-alanine and/or a derivative of β-alanine, and (b) at least one agent that modulates the NMDA pathway.

The compositions, formulations, and food or beverage products of the present invention are prepared with effective amounts of (a) and (b). The effective amount of (a) for daily dosage can range from about 25 mg/kg body weight to about 91 mg/kg body weight per day. Preferably, the effective amount of (a) for daily dosage is between about 25 mg/kg body weight to about 285 mg/kg body weight.

The amounts of (a) and (b) in the compositions, formulations, and food or beverage products of the present invention can be provided in a ratio of (a) to (b). Exemplary ratios of (a) to (b) include, for example, 1:5 to 1:15, 1:1 to 1:80, and 2:1 to 1500:1.

In instances in which the compositions, formulations, and food or beverage products of the present invention are provided in a solid form, the preparation can include from about 4 to 88% w/w of (a) and from 0.0005 to 45% w/w of (b).

In instances in which the compositions, formulations, and food or beverage products of the present invention are provided in a liquid form, the preparation can include from 5 to 90% w/v of (a) and from 0.005 to 60% w/v of (b).

It should also be appreciated that (a) and (b) in the compositions, formulations, and food or beverage products can be present in admixture. The admixture can be processed to provide particles of an average particle size. As used herein, "particle size" refers to the diameter of the particle. "Average particle size" means that at least 50% of the particles in a sample will have the specified particle size. For example, at least a portion of the admixture can be fine-milled to provide an average particle size of between 50 nm and 2 μm. The use of dry milling techniques, combined with excipients and polymers, to form fine-milled particles improves flow and dispersibility, stability, resistance to moisture, bioavailability, and dissolution/release properties of the active agents. Additionally, (a) and (b) can be administered in the same preparation or different preparation, and can be administered together, in rapid succession, or at intervals.

In some instances, (a) and (b) can be provided as commercially supplied raw materials. Alternatively, (a) and/or (b) may be preprocessed by routine methods. Examples of such preprocessing methods include, but are not limited to agglomeration, air suspension, chilling, air suspension drying, balling, coacervation, chilsonation, comminution, compression, pelletization, cryopelletization, extrusion, granulation, homogenization, inclusion compoundation, lyophilization, liposomal processing, lecithinization, melting, mixing, molding, pan coating, solvent dehydration, sonication, spheronization, spray chilling, spray congealing, spray drying, or other techniques known in the art according to the desired dosage form. In some instances, (a) or (b) can be post-processed (e.g., to improve the shelf life or stability of the active agents). For example, the methods disclosed in U.S. Patent Application Publication No. 2011/0250340 (incorporated herein by reference in its entirety) can be used to prepare a shelf stable liquid form of the active agent β-alanine.

The compositions and formulations for use in accordance with the present invention can be prepared in a conventional manner using one or more physiologically acceptable (e.g., pharmaceutically or nutritionally acceptable) carriers, diluents, or excipients. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. Routine methods useful for formulating preparations are known in the art and can be found in, for example, Remington's Pharmaceutical Sciences (Gennaro, ed., Williams & Wilkins, Baltimore, Md.).

The compositions and formulations comprising (a) and (b) (or their physiologically acceptable derivatives, e.g., salts and/or solvates) can be prepared for administration by various routine methods.

Examples of suitable administration methods include parenteral, e.g., intravenous, subcutaneous, intramuscular, intracranial, intraorbital, ophthalmic, intraventricular, intracapsular, intraspinal, intracisternal, intraperitoneal, transmucosal, or administration may be oral. The active agents can be prepared in various ways, depending on the route of administration, as will be apparent to those skilled in the art.

Solid oral preparations for administration can include, for example, tablets or capsules or powders, prepared by conventional means with pharmaceutically or nutritionally acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art.

Liquid oral preparations for administration can include, for example, solutions, syrups or suspensions, or they can be presented as a dry product for constitution with water or other suitable vehicle before use. Such liquid preparations can be prepared by conventional means with pharmaceutically or nutritionally acceptable additives such as suspending agents (for example, sorbitol syrup, cellulose derivatives or hydrogenated edible fats); emulsifying agents (for example, lecithin may serve this function, or acacia); nonaqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring and sweetening agents as appropriate. Preparations for oral administration can be formulated to give controlled release or sustained release of the active agents. Sustained released formulations are a conventional solution to the problem of rapid systemic clearance, as is well known to those of skill in the art (See, e.g., "Remington's Pharmaceutical Sciences," Philadelphia College of Pharmacy and Science, 19th Edition, 1995). Osmotic delivery systems are also recognized methods for sustained drug delivery (See, e.g., Verma et al., *Drug Dev. Ind. Pharm.* 2000, 26:695-708). In a particular example, a composition or formulation of the present invention can be formulated for sustained release of β-alanine, as described in U.S. Patent Application Publication No. 2009/0220575, incorporated herein by reference in its entirety.

Tablets or lozenges, for example, can be prepared in a conventional manner for buccal or sublingual administration of a composition or formulation of the present invention.

The nutritional compositions of the present invention can be prepared in any suitable form, e.g., a powder, a drink, a food bar, a cookie, a granule, a tablet, a pill, a capsule, a softgel, a gelcap, a solution, a salve, a lotion, or a suspension.

The food or beverage products of the present invention can be prepared in any suitable form, for example, in the form of a fruit or juice products, concentrates of fruit or juice products, lemonades, dairy products, frozen confectionary products, baked goods, spreads, margarine, butter, peanut butter, honey, pasta products, cereal products, ready-to-serve-dishes, frozen food, tinned food, syrups, sauces, fillings, dips, chewing gums, sherbet, spices, cooking salt, and instant drink powders.

A beverage product of the present invention may be in the form of a powder or liquid concentrate to be mixed with a suitable liquid, e.g., water or milk, before consumption, or a ready-to-drink beverage (i.e., a beverage in liquid form ready to be consumed without adding liquid). A beverage of the present invention may be carbonated by any suitable method known in the art.

The food or beverage product of the present invention can also be prepared with one or more additional agents commonly used in the food or beverage industry. Exemplary agents include, but are not limited to, thickeners, coloring agents, bulking agents, polyols, xylitol, mannitol, maltitol, preservatives, sodium or potassium benzoate, sodium or calcium carbonate, antioxidants, ascorbic acid, carotenoids, tocopherols or polyphenols, mono-, oligo- or polysaccharides, glucose, fructose, sucrose, soyoligosaccharides, xylooligosaccharides, galactooligosaccharides, artificial or natural non- or low-caloric sweeteners, aspartame, sucralose, acesulfame potassium, acidifiers in the form of edible acids, citric acids, acetic acid, lactic acid, apipic acid, flavors, emulsifiers, diluents, maltodextrin, wetting agents, glycerol, stabilizers, coatings, isotonic agents, and absorption promoting or delaying agents.

The compositions and formulations of the present invention can be prepared for parenteral administration via injection, for example, via bolus or continuous infusion. Injected formulations can be presented in unit dosage form, such as ampoules or in multi-dose containers, preferably with an added preservative. The preparations can be formed as suspensions, solutions or emulsions in oily or aqueous vehicles, and can contain formulatory agents such as suspending, stabilizing and/or dispersing agents. Alternatively, the active agents can be in powder form for constitution with a suitable vehicle, for example, sterile pyrogen-free water, before use.

The compositions and formulations of the present invention can be prepared for use in rectal compositions such as suppositories or retention enemas, for example, containing conventional suppository bases such as cocoa butter or other glycerides.

The compositions and formulations of the present invention can also be prepared as a depot preparation. Depot preparations are long acting formulations that can be administered via implantation (e.g., subcutaneously or intramuscularly) or via intramuscular injection. For example, the preparations can be formulated with suitable polymeric or hydrophobic materials (for example as an emulsion in an acceptable oil) or ion exchange resins, or as sparingly soluble derivatives, for example, as a sparingly soluble salt.

Because some of the active agents of the compositions, formulations, and food or beverage products of the present invention may act in the central nervous system, delivery techniques can be tailored to allow the preparation to cross the blood-brain barrier to increase the ability of the active agents to cross the blood-brain barrier. Examples of suitable techniques can be found in Begley, J. Pharm. Pharmacol., 48:136-146, 1996, incorporated herein by reference in its entirety. Alternatively, active agents of the present invention can be modified (e.g., chemically) using methods known in the art to facilitate their entry into the CNS.

In some instances, it can be desirable to deliver a composition or formulation directly to the nervous system using techniques such as intraventricular injection (Kordower et al., Exp. Neurol., 124:21-30, 1993) or installation of an osmotic pump (e.g., an Alzet® pump), for example. Another exemplary technique is to surgically place an Omaya reservoir-shunt with in-line filter into the cisternal space. A composition or formulation in an appropriate excipient (e.g., phosphate-buffered saline) is instilled into the shunt by injection on a prescribed basis.

For administration by inhalation, a composition or formulation of the present invention can be delivered, for example, as an aerosol spray with the use of a suitable propellant, for example, dichlorodifluoromethane, trichlorofluoromethane, dichlorotetrafluoroethane, carbon dioxide, or other suitable gas. Other suitable methods of nasal delivery known in the art can be used, including those that facilitate delivery of a predetermined dosage.

The preparations can be presented in a pack or dispenser device, which may contain one or more unit dosage forms containing the active agents. The pack may, for example, comprise metal or plastic foil, such as a blister pack. The pack or dispenser device can be accompanied by instructions for administration (e.g., FDA approved labeling information).

As apparent to those skilled in the art, it is not necessary for all of the active agents of a composition or formulation to be administered in the same excipient, in the same form, or delivered at precisely the same time during a day. However, the active agents should be administered so they are present in the treated subject at the same time (e.g., present in a cell that is the target of treatment), and thus, one preparation, including all active agents, is generally provided in a convenient dosage form.

This condition of treatment can be ascertained by assaying the appropriate body fluid (e.g., blood, plasma, serum, or cerebrospinal fluid) or body tissue (e.g., skeletal muscle, adipose tissue, or connective tissue) for the presence of components of a formulation or their metabolites. When monitoring the concentrations of active agents, attention must be paid to differential accumulation of agents and/or their metabolites in the particular body fluid being tested.

In some instances, the active agents can be co-administered. As used herein, "co-administered" and/or "co-administration" refer to the administration of more than one active agent in the course of a coordinated treatment to achieve an improved clinical outcome. Such co-administration may also be coextensive; that is, occurring during overlapping periods of time.

Veterinary Applications

The compositions, formulations, and food or beverage products of the present invention can be used in veterinary applications in instances in which an animal would benefit from enhanced physical performance (e.g., training procedures for hunting dogs, guide dogs, police dogs, thoroughbred race horses, etc., or animals used in the movie industry). Animals that may benefit from enhanced physical performance include pets (e.g., dogs, cats, birds, fish, guinea pigs, rabbits, hares, ferrets), farm animals (fish, pigs, horses, cattle, sheep, goats, and poultry), and show animals (e.g., tigers, bears, lions, elephants, etc.).

All-Natural Compositions

The compositions, formulations, and food or beverage products of the present invention can be prepared as an "all-natural" preparation where each of the ingredients (e.g., active agents, etc.) is derived from a natural source (plant, animal, etc.) in a substantially unmodified form, i.e., the form in which the material exists in its natural origin. These ingredients may be obtained from their natural source using extraction or other separation means. The ingredients of the preparations may be organic or aqueous extracts and/or minerals and electrolytes, or fermentation products. Examples of suitable natural ingredients that can be used as active agents and additives for the preparations of the present invention will be apparent to those skilled in the art.

Methods of Use

It will be apparent to those skilled in the art that the compositions, formulations, and food or beverage products of the present invention can be administered as part of a variety of methods, e.g., methods of enhancing physical performance in a human or animal, methods of reducing paraesthesia in a human or animal (e.g., reducing intolerable paraesthesia in the human or animal to a tolerable level), methods of improving a human or animal's tolerance and compliance to higher doses of β-alanine, thereby reducing the length of time it takes to achieve peak effect of β-alanine on physical performance in the human or animal (e.g., reducing the time it takes to achieve peak effect of β-alanine on physical performance in a human or animal by up to 85% from between 4 and 6 weeks to between 4 and 6 days). It is to be understood that any of the active agents disclosed herein or apparent to skilled in the art based on such disclosure can be used as active agents in the foregoing methods of the present invention. It should also be understood that the active agents can be employed in the methods in any combination desired.

An exemplary composition, formulation, or food or beverage product that can be administered in a method of the present invention comprises (a) β-alanine or a derivative of β-alanine; and (b) at least one agent that modulates the N-methyl D-aspartate (NMDA) pathway.

An exemplary method of the present invention is a method of enhancing physical performance in a human or animal comprising administering to the human or animal an effective amount of (a) β-alanine or a derivative of β-alanine; and an effective amount of (b) at least one agent that modulates the N-methyl D-aspartate (NMDA) pathway.

Another exemplary method of the present invention is a method of reducing β-alanine-induced paraesthesia in a human or animal (e.g., reducing intolerable β-alanine-alanine-induced paraesthesia in the human or animal to a tolerable level) comprising administering to the human or animal an effective amount of (a) β-alanine or a derivative of β-alanine; and an effective amount of (b) at least one agent that modulates the N-methyl D-aspartate (NMDA) pathway.

Yet another exemplary method of the present invention is a method of improving tolerance and compliance to higher doses of β-alanine so as to reduce the time it takes to achieve peak effect of β-alanine on physical performance in a human or animal comprising administering to the human or animal an effective amount of (a) β-alanine or a derivative of β-alanine; and an effective amount of (b) at least one agent that modulates the N-methyl D-aspartate (NMDA) pathway, wherein the at least one agent that modulates the NMDA pathway improves tolerance and compliance to higher doses of β-alanine, thereby reducing the length of time it takes to achieve peak effect of β-alanine on physical performance in the human or animal % (e.g., the length of time it takes to achieve peak effect of β-alanine on physical performance is reduced from 4-6 weeks to 4-6 days, i.e., reduced by up to about 85%).

For clarity, it is to be understood that it is within the scope and spirit of the present invention to employ one or more of component (a) and/or one or more of component (b) together in a composition, formulation or food or beverage product of the present invention and associated methods. As used herein, "one or more" includes any or all of the possible combinations that can be derived using components (a) and/or (b), and in any combination desired. As used herein, "combination" is to be interpreted broadly such that the combination can include multiple forms of β-alanine in combination with each other or with β-alanine and/or a derivative of β-alanine, as well as multiple derivatives of β-alanine, if desired. It will be apparent to those skilled in the art that this broad interpretation of combination applies equally to the agents that modulate the NMDA pathway.

The active agents (a) and (b) can be present in admixture in the compositions, formulations, and food or beverage products administered in the methods of the present invention. The active agents (a) and (b) can also be chemically linked together in the compositions, formulations, and food or beverage products of the present invention, for example via a covalent bond (e.g., in the form of a dipeptide comprising (a) and (b), e.g., β-alanyl-L-theanine) or an ionic bond (e.g., in the form of a salt comprising (a) and (b), e.g., β-alanine-L-theanate) that is broken upon administration of the composition, formulation, and food or beverage product to a human or animal in such a way that both (a) and (b) impart a therapeutic effect to the human or animal. Any suitable method of administration disclosed herein (e.g., orally) or apparent to those skilled in the art can be used to administer the compositions, formulations, and food or beverage products in the methods of the present invention.

The compositions, formulations, and food or beverage products administered in the methods of the present invention enhance physical performance in a human or animal.

The compositions, formulations, and food or beverage products administered in the methods of the present invention do not elicit intolerable paraesthesia (e.g., moderate or severe paraesthesia typically elicited by administration of high doses of β-alanine).

The compositions, formulations, and food or beverage products administered in the methods of the present invention improve compliance with and tolerance of higher doses of β-alanine (or a derivative of β-alanine), thereby permitting usage of higher doses of β-alanine when compared to β-alanine administered alone.

The compositions, formulations, and food or beverage products administered in the methods of the present invention reduce the length of time it takes to achieve effect (e.g., peak effect) of β-alanine on physical performance (e.g., the time it takes to achieve peak effect of β-alanine on physical performance is reduced from between four and six weeks to between four and six days, i.e., a reduction of up to about 85% of the time it takes to achieve peak effect of β-alanine on physical performance compared to β-alanine administered alone in a traditional manner).

Those skilled in the art will appreciate that the advantages and benefits of the compositions, formulations, and food or beverage products of the present invention can be measured both subjectively and objectively in a variety of suitable ways. For example, carnosine concentrations in human skeletal muscle generally range between 15-40 mmol/kg dry weight. The reduction in the length of time it takes to achieve effect of β-alanine on physical performance in a human or animal can be measured by assaying the concentration of β-alanyl-L-histidine (carnosine) dipeptides directly in the skeletal muscle tissue or by assaying the activity of carnosinasel (CN1) in the serum (an indirect measure shown to correlate well with skeletal muscle carnosine concentration) of the human or animal. Alternatively, the pharmacokinetics of an acute, orally administered β-alanine dose may be obtained by assaying the concentration of β-alanine in the blood plasma and urine. Peak effect of β-alanine on physical performance in the human or animal is typically achieved when the baseline skeletal muscle β-alanyl-L-histidine (carnosine) dipeptides concentration increases by a minimum of ~10-15 mmol/kg dry weight.

It will be appreciated by those skilled in the art that measurable benefit (e.g., ergogenic benefit) of β-alanine is typically achieved when the amount of carnosine synthesized in the human or animal reaches a level that is about 40% to about 60% greater than a baseline level of carnosine synthesized. For example, baseline carnosine levels in the human or animal can be measured once or at successive intervals before administration of a composition, formulation or food or beverage product of the present invention. Carnosine levels can then be measured at successive intervals (e.g., daily, weekly or monthly, for example) in the human or animal after administration of the composition, formulation or food or beverage product of the present invention. Carnosine levels measured at each successive interval are measured and then compared to the baseline. When the amount of carnosine synthesized in the human or animal reaches a level that is about 40% to about 60% greater than baseline, an effect of β-alanine (e.g., on physical performance) is achieved. It is expected that the carnosine levels will be about 40% greater than baseline in as few as 4-6 days of administration of a composition, formulation, or food or beverage product of the present invention.

During the course of work described herein, the inventors demonstrated that the compositions, formulations, and food or beverage products of the present invention comprising β-alanine and at least one agent that modulates the NMDA pathway are useful for improving tolerance and compliance to higher doses of β-alanine. Specifically, the change in 100 mm anchored VAS ratings for paraesthesia (burning, tingling, pricking and flushing sensations) was evaluated utilizing an acute, single-blinded, latin square crossover design comparing β-alanine to β-alanine combined with two doses of an agent that modulates the NMDA pathway agent (one dose at a 1:6 ratio and another at 1:12 ratio of β-alanine to the agent that modulates the NMDA pathway). The visual analog scale (VAS) is a an anchored, standardized 100 mm or 150 mm scale has been demonstrated to be a valid, reliable and methodologically sound instrument for quantitative assessment of pain, discomfort or other psychometric parameters. A minimum clinically significant difference in VAS rating for pain or paraesthesia appears to range from 13 mm to 16 mm with a 95% confidence interval. (See e.g., Gallagher, et al., Am J Emerg Med. 2002; 20(4):287-90; Bouhassira, et al., Pain. 2004; 108(3):248-57; Poliakov, et al. Eur J Pain. 2011 November; 15(10):1015-22; and Eisenberg, et al. Eur J Pain. 1998; 2(4):321-327). VAS rating instruments have also been deemed specific and sensitive to detect the effects of an intervention on paraesthesia and neuropathic pain. Evidence in support of the present invention was obtained by evaluating the change in 100 mm anchored VAS ratings for parasthesias (burning, tingling, itching, pricking and flushing sensations) utilizing an acute, single-blinded, latin square cross-over design comparing β-alanine to β-alanine plus two doses of an NMDA modulating agent (one dose at 1:6 ratio and another at 1:12 ratio of β-alanine to the NMDA modulating agent. Notably, the individuals' anchored 100 mm VAS scores, on a scale from 0-100 mm, changed from 60 mm-90 mm (when ingesting β-alanine alone) to about a 10 mm-30 mm (when ingesting β-alanine and at least one agent that modulates the NMDA pathway).

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Figure 2:
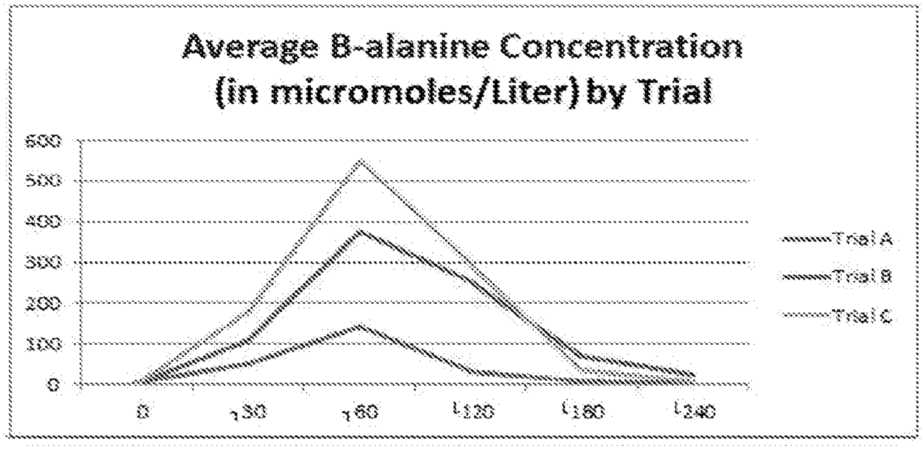
FIG. 2 is a line graph showing the average plasma β-alanine concentration (in micromoles/Liter) over time by trial upon co-administration of β-alanine and at least one agent that modulates the NMDA pathway to healthy men in each trial.
Figure 3:
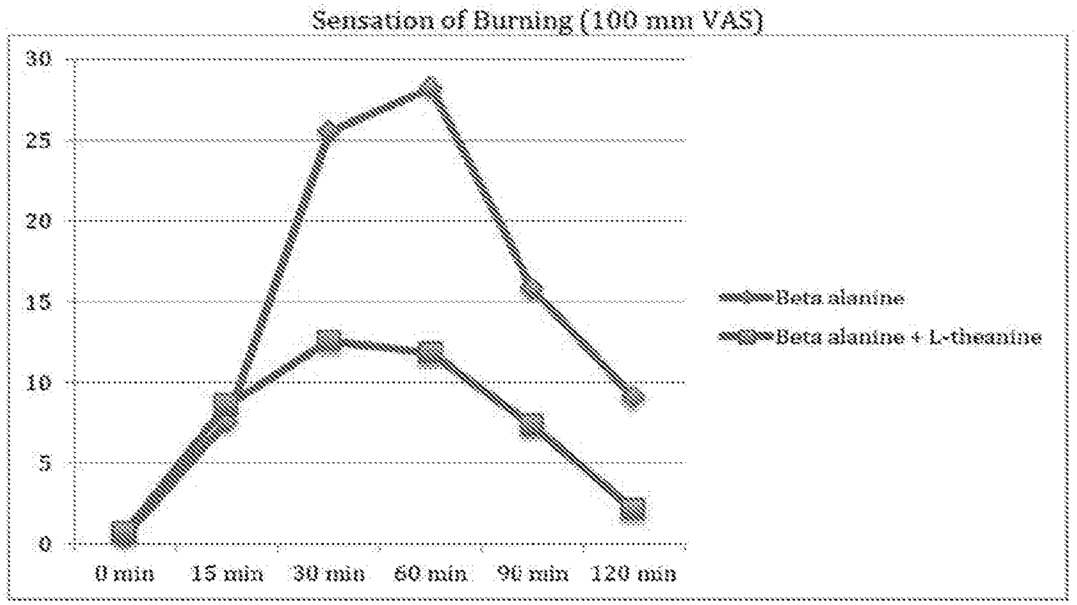
FIG. 3 is a line graph depicting data from anchored 100 mm VAS on N=10 subjects, comparing subjective sensation of overall discomfort (e.g., sensation of burning) from an 8 gram acute oral dose of β-alanine alone compared to 8 grams of β-alanine together with 600 mg of L-theanine.
Figure 4:
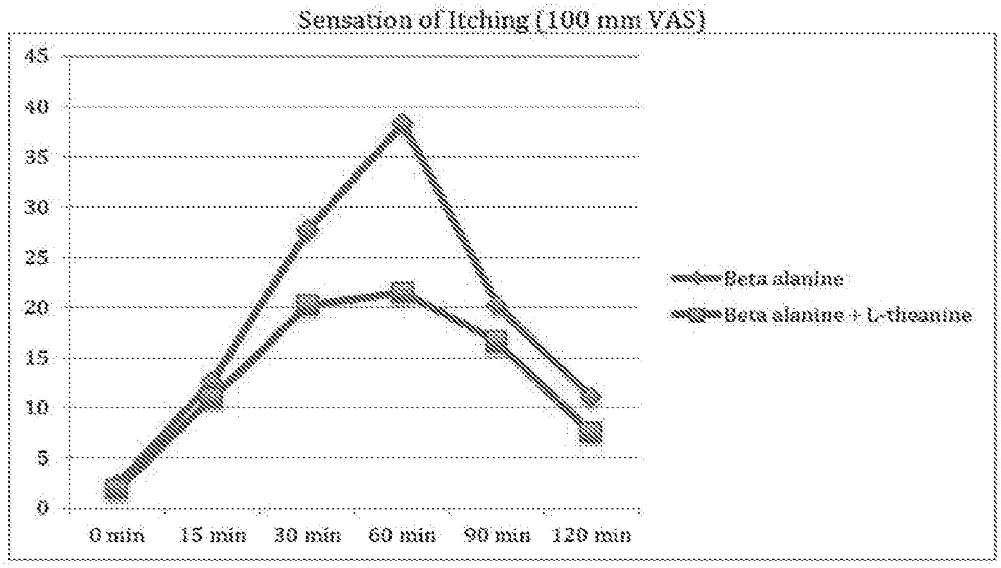
FIG. 4 is a line graph depicting data from anchored 100 mm VAS on N=10 subjects, comparing subjective sensation of overall discomfort (e.g., sensation of itching) from an 8 gram acute oral dose of β-alanine alone compared to 8 grams of β-alanine together with 600 mg of L-theanine.
Figure 5:
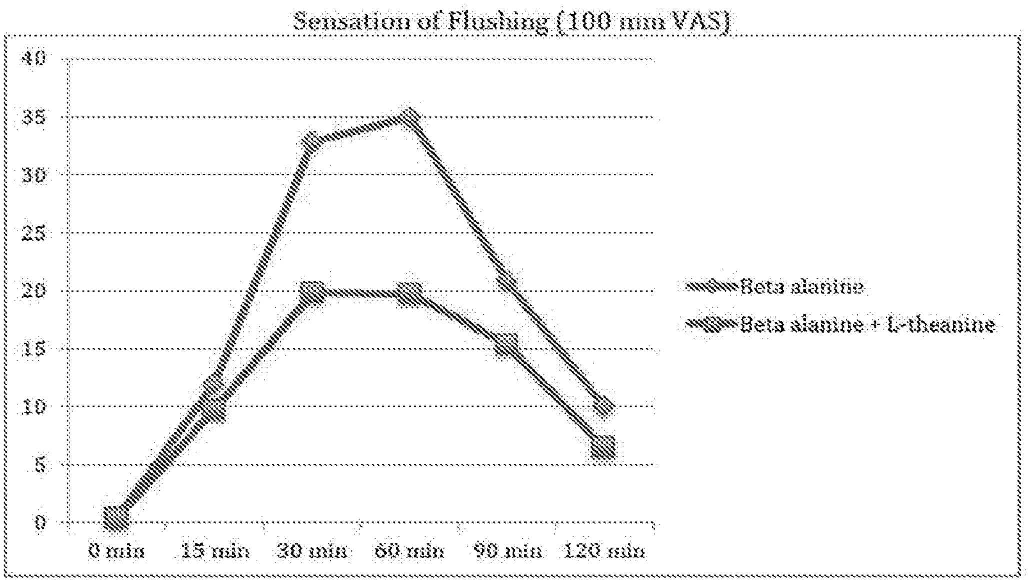
FIG. 5 is a line graph depicting data from anchored 100 mm VAS on N=10 subjects, comparing subjective sensation of overall discomfort (e.g., sensation of flushing) from an 8 gram acute oral dose of β-alanine alone compared to 8 grams of β-alanine together with 600 mg of L-theanine.
Figure 6:
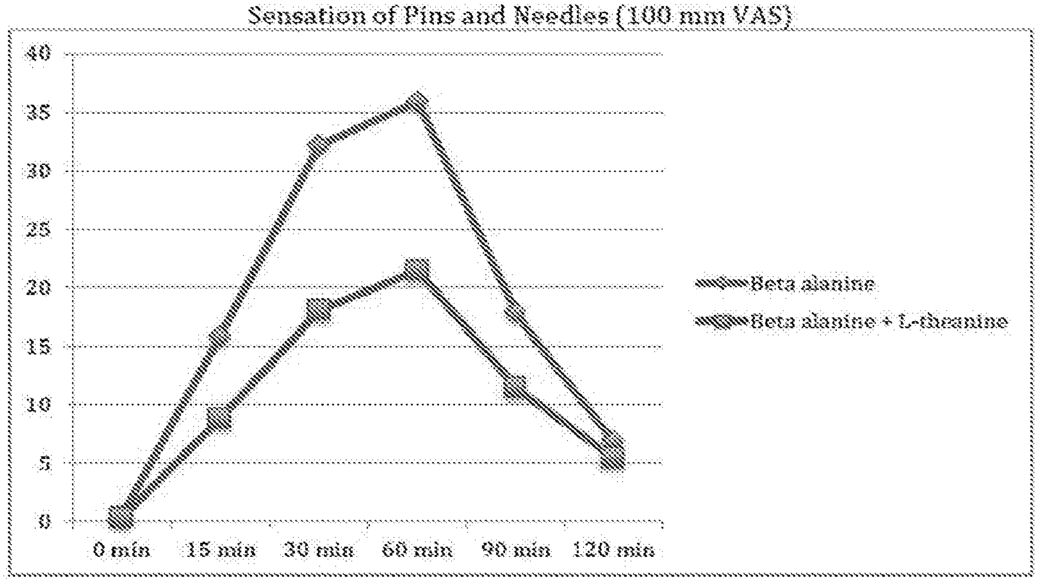
FIG. 6 is a line graph depicting data from anchored 100 mm VAS on N=10 subjects, comparing subjective sensation of overall discomfort (e.g., sensation of pins and needles) from an 8 gram acute oral dose of β-alanine alone compared to 8 grams of β-alanine together with 600 mg of L-theanine.

During the course or work described herein, a pilot study was conducted in 3 healthy men to demonstrate that co-administration of β-alanine and at least one agent that modulates the NMDA pathway improves tolerance and compliance to higher doses of β-alanine. Each subject completed three trials, labeled "A", "B", and "C" using a Latin square design (i.e. subject 1 completed trials in ABC order, subject 2 completed trials in BCA order, and subject 3 completed trials in CAB order). Trial A consisted of the oral ingestion of 3.2 g β-alanine, trial B consisted of 6.4 g β-alanine+500 mg L-theanine, trial C consisted of 6.4 g β-alanine+1000 mg L-theanine. Blood samples were drawn into lithium heparin tubes at baseline (time 0), 30 min, 1 hr, 2 hr, 3 hr, 4 hr post ingestion, spun in a clinical centrifuge for 15 minutes, and processed to obtain plasma. Plasma was immediately frozen at −80 degrees C. until analysis for β-alanine by gas chromatography-mass spectrometry. Results indicated a significant increase in plasma β-alanine from the 3.2 g to both 6.4 g doses, as well as a significant reduction in symptoms of paraesthesia in all subjects when L-theanine was co-ingested. Notably, the net retention of β-alanine (measured via subtracting the urinary loss of β-alanine during the period of collection from the area-under-the-plasma-curve) was greatest in trial B (see FIG. 2 and Table 1).

TABLE 1

| Subject | Trial | Net Loss (uMol) |
|---|---|---|
| 1 | A | 10167.5 |
| | B | 35843.2 |
| | C | 29004.5 |
| 2 | A | 8606.6 |
| | B | 57842.4 |
| | C | 69873.9 |
| 3 | A | 8749.3 |
| | B | 14425.6 |
| | C | 45274.7 |
| Mean (SD) | A | 9174.5 (862.96) |
| | B | 36037.1 (21709.05) |
| | C | 48051.0 (20575.66) |

Example 2

A proof of concept study was carried out in 10 human subjects to evaluate the effect of a composition comprising component (a) together with one agent from component (b) on reducing the paresthetic response associated with β-alanine administration. The subjects' sensory responses were measured with an anchored 100 mm VAS (see FIGS. 3-6). As is shown in FIGS. 3-6, the composition significantly improved subject tolerance to large doses of β-alanine, for example, by reducing the paraesthetic response (i.e., the composition comprising β-alanine and L-theanine significantly decreased the subjects' sensations of overall discomfort from burning (FIG. 3), itching (FIG. 4), flushing (FIG. 5), and pins and needles (FIG. 6) compared to the administration of the same dose of β-alanine alone).

Example 3

Figure 7:
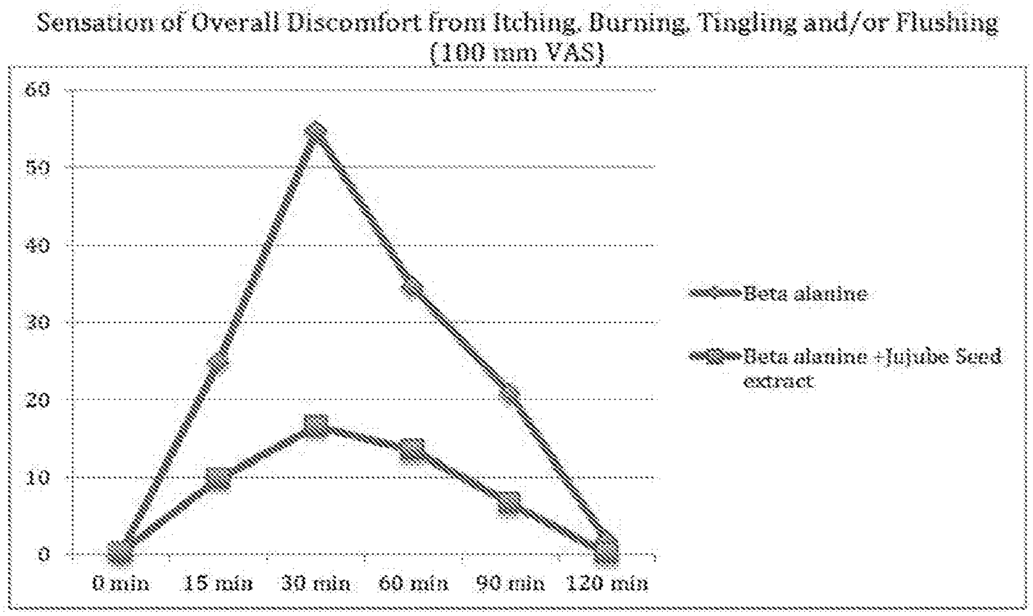
FIG. 7 is a line graph depicting data from anchored 100 mm VAS on N=6 subjects, comparing subjective sensation of overall discomfort (e.g., sensation of overall discomfort from burning, itching, flushing and/or tingling) from an 8 gram acute oral dose of β-alanine alone compared to an 8 gram dose of β-alanine together with 200 mg of *Ziziphus jujube* var. *spinosa* extract (also known as wild *jujube* seed extract).

Another pilot study was conducted in 6 human subjects to evaluate the effect of a composition comprising of component (a) together with one botanical agent from component (b) (*Ziziphus jujuba* var. *spinosa* extract) on reducing the paresthetic response associated with β-alanine administration. The subjects' sensory responses were measured with an anchored 100 mm VAS (see FIG. 7). As is shown in FIG. 7, the composition significantly improved subject tolerance to large doses of β-alanine, for example, by reducing the paraesthetic response (i.e., the composition comprising β-alanine and *Ziziphus jujube* var. *spinosa* extract significantly decreased the subjects' sensations of overall discomfort due to burning, itching, flushing, and/or tingling compared to the administration of the same dose of β-alanine alone).

Example 4

Figure 8:
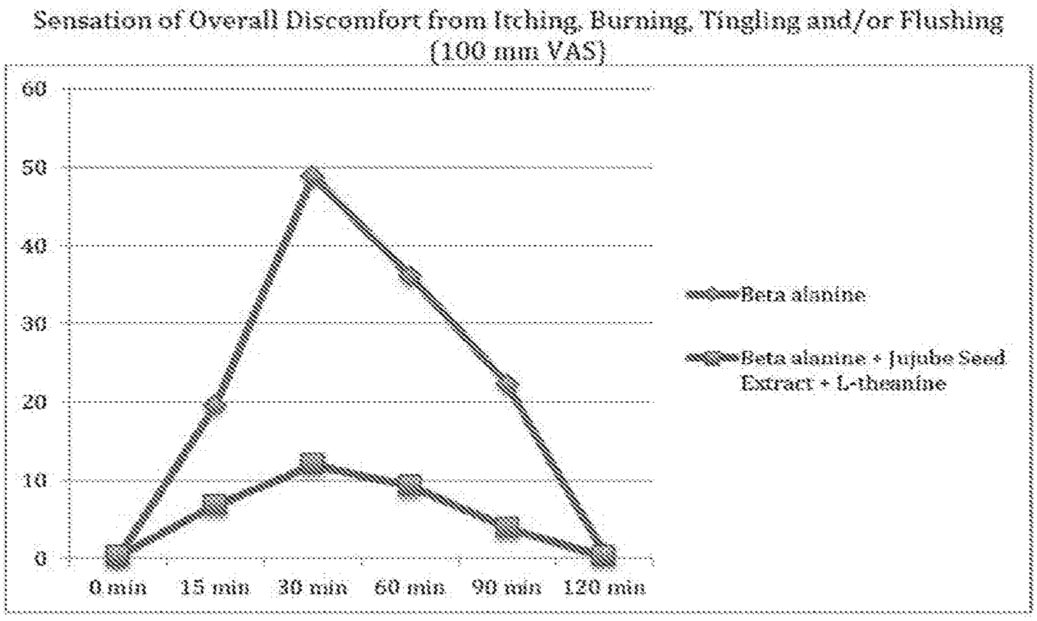
FIG. 8 is a line graph depicting data from anchored 100 mm VAS on N=5 subjects, comparing subjective sensation of overall discomfort (e.g., sensation of overall discomfort from burning, itching, flushing and/or tingling) from an 8 gram acute oral dose of β-alanine alone compared to an 8 gram dose of β-alanine together with 150 mg of *Ziziphus jujube* var. *spinosa* extract and 200 mg L-theanine.

An additional pilot study was conducted in 5 human subjects to evaluate the effect of a composition comprising of component (a) together with two agents from component (b) (*Ziziphus jujuba* var. *spinosa* extract and L-theanine) on reducing the overall discomfort/paresthetic response associated with β-alanine administration. The subjects' sensory responses were measured with an anchored 100 mm VAS (SEE FIG. 8). As is shown in FIG. 8, the composition significantly improved subject tolerance to large doses of β-alanine, for example, by reducing the paresthetic response (i.e., the composition comprising β-alanine, *Ziziphus jujube* var. *spinosa* extract, and L-theanine significantly decreased the subjects' sensations of overall discomfort due to burning, itching, flushing, and/or tingling compared to the administration of the same dose of β-alanine alone).

What is claimed is:

1. A composition comprising (a) an effective amount of β-alanine or a derivative of β-alanine; and (b) an amount of at least one agent that modulates the N-methyl D-aspartate (NMDA) pathway, wherein the amount of (b) is effective to reduce intolerable paraesthesia caused by (a) to a tolerable level, wherein the at least one agent that modulates the NMDA pathway is selected from the group of agents consisting of L-glycine, botanical rhizome preparations or extracts selected from the group consisting of Acorus gramineus, *Polygala tenuifolia, Celastrus paniculatus*, and, *Zizyphus jujuba* var. *spinosa*, and combinations thereof, or wherein the at least one agent that modulates the NMDA pathway is an NMDA receptor antagonist selected from the group consisting of dextromethorphan, kynurenic acid, histogranin, memantine, meperidine, methadone, phencyclidine, and combinations thereof, and wherein the composition is a solid and comprises 4 to 88% w/w of (a) and from 0.0005 to 45% w/w of (b) or is a liquid and comprises from 5 to 90% w/v of (a) and from 0.005 to 60% w/v of (b), and wherein the derivative of beta alanine is selected from the group consisting of N-acetyl-β-alanine, fluorinated methyl β-alanine, 3-amino-3-fluoromethylpropionic acid, a β-alanine ester, a β-alanine amide, a β-alanine salt, and β-alanine nitrate.

2. The composition of claim 1, wherein the composition is a solid and comprises 4 to 88% w/w of (a) and from 0.0005 to 45% w/w of (b).

3. The composition of claim 1, wherein the composition is a liquid and comprises from 5 to 90% w/v of (a) and from 0.005 to 60% w/v of (b).

4. The composition of claim 1, further comprising a pharmaceutically acceptable carrier, diluent, or excipient.

5. The composition of claim 1, wherein the composition is a powder.

6. The composition of claim 1, wherein (a) comprises an effective amount of β-alanine.

7. A composition comprising (a) an effective amount of β-alanine or a derivative of β-alanine; and (b) an amount of at least one agent that modulates the N-methyl D-aspartate (NMDA) pathway, wherein the amount of (b) is effective to reduce intolerable paraesthesia caused by (a) to a tolerable level, wherein the at least one agent that modulates the NMDA pathway comprises L-theanine and *Zizyphus jujuba* var. *spinosa* botanical rhizome extract or preparation, wherein the composition is a solid and comprises 4 to 88% w/w of (a) and from 0.0005 to 45% w/w of (b) or is a liquid and comprises from 5 to 90% w/v of (a) and from 0.005 to 60% w/v of (b), and wherein the derivative of beta alanine is selected from the group consisting of N-acetyl-β-alanine, fluorinated methyl β-alanine, 3-amino-3-fluoromethylpropionic acid, a β-alanine ester, a β-alanine amide, a β-alanine salt, and β-alanine nitrate.

8. The composition of claim 7, wherein (a) comprises an effective amount of β-alanine.

9. A composition comprising (a) an effective amount of β-alanine or a derivative of β-alanine; and (b) an amount of at least one agent that modulates the N-methyl D-aspartate (NMDA) pathway, wherein the amount of (b) is effective to reduce intolerable paraesthesia caused by (a) to a tolerable level, wherein the at least one agent that modulates the NMDA pathway comprises L-theanine, *Celastrus paniculatus* botanical rhizome preparation or extract, and *Zizyphus jujuba* var. *spinosa* botanical rhizome preparation or extract, wherein the composition is a solid and comprises 4 to 88% w/w of (a) and from 0.0005 to 45% w/w of (b) or is a liquid and comprises from 5 to 90% w/v of (a) and from 0.005 to 60% w/v of (b), and wherein the derivative of beta alanine is selected from the group consisting of N-acetyl-β-alanine, fluorinated methyl β-alanine, 3-amino-3-fluoromethylpropionic acid, a β-alanine ester, a β-alanine amide, a β-alanine salt, and β-alanine nitrate.

10. The composition of claim 9, wherein (a) and (b) are present at a weight ratio of between 1:1 to 1:80.

11. The composition of claim 9, wherein (a) comprises an effective amount of β-alanine.

* * * * *